United States Patent
Zhao et al.

(10) Patent No.: US 9,453,028 B2
(45) Date of Patent: *Sep. 27, 2016

(54) PROTEIN KINASE C INHIBITORS AND USES THEREOF

(71) Applicant: Rigel Pharmaceuticals, Inc., South San Francisco, CA (US)

(72) Inventors: Haoran Zhao, Foster City, CA (US); Rao Kolluri, Foster City, CA (US); Carlos Valdez, San Ramon, CA (US); Kin Tso, San Francisco, CA (US); Rajinder Singh, Belmont, CA (US); John Ramphal, Union City, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/754,415

(22) Filed: Jun. 29, 2015

(65) Prior Publication Data

US 2015/0376203 A1 Dec. 31, 2015

Related U.S. Application Data

(63) Continuation of application No. 13/760,666, filed on Feb. 6, 2013, now Pat. No. 9,095,593, which is a continuation of application No. 12/687,054, filed on Jan. 13, 2010, now Pat. No. 8,394,951.

(60) Provisional application No. 61/145,021, filed on Jan. 15, 2009, provisional application No. 61/147,353, filed on Jan. 26, 2009.

(51) Int. Cl.
| | |
|---|---|
| *C07D 345/00* | (2006.01) |
| *C07D 517/00* | (2006.01) |
| *C07D 498/04* | (2006.01) |
| *C07D 498/14* | (2006.01) |
| *A61K 31/5383* | (2006.01) |

(52) U.S. Cl.
CPC ......... *C07D 498/04* (2013.01); *A61K 31/5383* (2013.01); *C07D 498/14* (2013.01)

(58) Field of Classification Search
CPC ............ A61K 31/5383; C07D 498/04; C07D 498/14
See application file for complete search history.

(56) References Cited

U.S. PATENT DOCUMENTS

| | | | |
|---|---|---|---|
| 2005/0234049 A1* | 10/2005 | Singh | C07D 403/12 514/224.2 |
| 2008/0287410 A1 | 11/2008 | Barbosa et al. | |
| 2008/0306099 A1 | 12/2008 | Li et al. | |

FOREIGN PATENT DOCUMENTS

| | | |
|---|---|---|
| CN | 1704404 | 12/2005 |
| CN | 1798748 | 7/2006 |
| CN | 101072556 | 11/2007 |
| WO | 2006129100 | 12/2006 |
| WO | 2007028445 | 3/2007 |
| WO | 2007124221 | 11/2007 |
| WO | 2007146981 | 12/2007 |
| WO | 2008024634 | 2/2008 |
| WO | 2009012421 | 1/2009 |

OTHER PUBLICATIONS

Connors et al., "Phase II Clinical Experience With the Novel Proteasome Inhibitor Bortezomib in Patients With Indolent Non-Hodgkin's Lymphoma and Mantle Cell Lymphoma," J. Clin Oncol. 3(26): (2005).
Foss, "Evolving therapy of peripheral T-cell lymphoma: 2010 and beyond," Ther. Adv Hem 2(3): 161-173 (2011).
Ramsay et al., "Chronic lymphoytic leukaemia—the role of the microenvironment pathogenesis and therapy," British Journal of Haematology 16: 15-24 (2013).
Robertson et al., "Phase II Study of Enzastaurin, a Protein Kinase C Beta Inhibitor, in Patients With Relapsed or Refractory Diffuse Large B-Cell Lymphoma," J. Clin Oncol. 25: 1741-1746 (2007).
Cywin et al. Discovery of potent and selective PKC-theta inhibitors. Bioorg Med Chem Lett., 17 (1):225-30 (2007).
Kluiver et al., "BIC and miR-155 are highly expressed in Hodgkin, primary mediastinal and diffuse large B cell lymphomas," J. Pathol, 207, 243-249 (2005).
Kluiver et al., "Regulation of pri-microRNA BIC transcription and processing in Burkitt lymphoma," Oncogene, 26, 3769-3776 (2007).
Querfeld et al., "The Selective Protein Kinase C Inhibitor Enzastaurin Induces Apoptosis in Cutaneous T-Cell Lymphoma Cell Lines through the AKT Pathway," J. Investigative Dermatology, 126, 1641-1647 (2006).
Traxler et al. 4-(Phenylamino)pyrrolopyrimidines: potent and selective, ATP site directed inhibitors of the EGF-receptor protein tyrosine kinase. J Med Chem. 39(12):2285-92 (1996).
Van Den Berg et al.,"High Expression of Micro-RNA BIC/ miR155 in All Subtype of Hodgkin Lymphoma" Blood (ASH Annual Meeting Abstracts), 104, Abstract 430 (2004).
Zhao et al., "Recent Progress in Indolylmalemimide Derivatives as Protein Kinase C Inhibitors," Chinese Journal of Organic Chemistry, 28 (10): 1676-1684 (2008).
Zimmermann et al. Phenylamino-pyrimidine(PAP)-derivatives:A new class of potent and highly selective PDGF-receptor autophosphorylation inhibitors. Bioorganic & Medicinal Chemistry Letters, 6:1221-1226 (1996).

\* cited by examiner

*Primary Examiner* — Jean Cornet
(74) *Attorney, Agent, or Firm* — Rudy J. Ng; Carol L. Francis; Bozicevic, Field & Franics LLP

(57) ABSTRACT

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions comprising these compounds, methods of using these compounds in the treatment of various diseases and disorders, processes for preparing these compounds and intermediates useful in these processes.

6 Claims, No Drawings

US 9,453,028 B2

PROTEIN KINASE C INHIBITORS AND USES THEREOF

CROSS-REFERENCE TO RELATED APPLICATIONS

This application is a continuation of U.S. patent application Ser. No. 13/760,666 filed on Feb. 6, 2013, which is a continuation of U.S. patent application Ser. No. 12/687,054 filed on Jan. 13, 2010, which claims priority benefit under 35 U.S.C. §119(e) to U.S. Provisional Patent Application No. 61/145,021, filed on Jan. 15, 2009 and U.S. Provisional Patent Application No. 61/147,353, filed on Jan. 26, 2009, which are incorporated by reference in their entireties.

BACKGROUND

Protein kinase C ("PKC") is a key enzyme in signal transduction involved in a variety of cellular functions, including cell growth, regulation of gene expression, and ion channel activity. The PKC family of isozymes includes at least 11 different protein kinases that can be divided into at least three subfamilies based on their homology and sensitivity to activators. Each isozyme includes a number of homologous ("conserved" or "C") domains interspersed with isozyme-unique ("variable" or "V") domains. Members of the "classical" or "cPKC" subfamily, PKC α, $β_i$, $β_{ii}$ and γ, contain four homologous domains (C1, C2, C3 and C4) and require calcium, phosphatidylserine, and diacylglycerol or phorbol esters for activation. Members of the "novel" or "nPKC" subfamily, PKC δ, ε, η and θ, lack the C2 homologous domain and do not require calcium for activation. Finally, members of the "atypical" or "aPKC" subfamily, PKC ζ and λ/ι, lack both the C2 and one-half of the C1 homologous domains and are insensitive to diacylglycerol, phorbol esters and calcium.

SUMMARY

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions comprising these compounds, methods of using these compounds in the treatment of various diseases and disorders, processes for preparing these compounds and intermediates useful in these processes.

Exemplary chemical structures are provided throughout the disclosure. By way of example, such compounds are represented by the following formula (I):

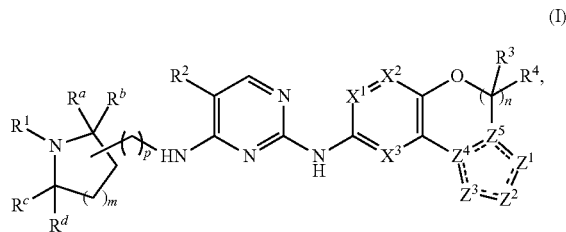

wherein $R^1$ is selected from hydrogen, alkyl, alkenyl, alkynyl, cycloalkyl, —C(O)O$R^{1a}$, —S(O)$R^{1b}$, and —S(O)$_2R^{1c}$; wherein each of $R^{1a}$, $R^{1b}$, and $R^{1c}$ is independently hydrogen, alkyl or phenyl-alkyl;

$R^a$, $R^b$, $R^c$ and $R^d$ independently are selected from hydrogen and alkyl;

m is an integer from one to five;

p is an integer from zero to six;

$R^2$ is selected from acyloxy, hydroxy, thiol, acyl, alkyl, alkoxy, substituted alkyl, substituted alkoxy, amino, substituted amino, aminoacyl, acylamino, azido, carboxyl, carboxylalkyl, cyano, halogen, nitro, aminoacyloxy, oxyacylamino, thioalkoxy, substituted thioalkoxy, —SO-alkyl, —SO-substituted alkyl, —SO-aryl, —SO-heteroaryl, —SO$_2$-alkyl, —SO$_2$— substituted alkyl, —SO$_2$-aryl, —SO$_2$-heteroaryl, and trihalomethyl;

$X^1$, $X^2$, and $X^3$ are CR$^5$ or one of $X^1$, $X^2$, and $X^3$ is N and rest are CR$^5$;

$R^5$ is selected from hydrogen, halogen, alkyl and substituted alkyl;

$R^3$ and $R^4$ are, for each occurrence, independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^3$ and $R^4$ together with the carbon atom to which they are attached form a carbocyclic or heterocyclic 4 to 8-membered ring;

n is an integer from one to three;

$Z^1$, $Z^2$, and $Z^3$ are selected from CR$^6$R$^{6a}$, N, O, and S;

$Z^4$ and $Z^5$ are selected from N, C, and CR$^6$;

$R^6$ is selected from hydrogen, halogen, alkyl and substituted alkyl;

$R^{6a}$ is selected from hydrogen, halogen, alkyl and substituted alkyl or is absent to satisfy valence requirements; and the dashed lines represent a single bond or double bond; or a salt or solvate or stereoisomer thereof.

DEFINITIONS

The following terms have the following meanings unless otherwise indicated. Any undefined terms have their art recognized meanings.

The term "alkyl" refers to a monoradical branched or unbranched saturated hydrocarbon chain, e.g., having from 1 to 40 carbon atoms, from 1 to 10 carbon atoms, or from 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR'R", wherein R' and R" may be the same or different and are chosen from hydrogen, optionally substituted alkyl, cycloalkyl, alkenyl, cycloalkenyl, alkynyl, aryl, heteroaryl and heterocyclic.

The term "alkylene" refers to a diradical of a branched or unbranched saturated hydrocarbon chain, usually having from 1 to 40 carbon atoms, more usually 1 to 10 carbon atoms and even more usually 1 to 6 carbon atoms. This term is—exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

The term "substituted alkylene" refers to an alkylene group as defined herein wherein one or more carbon atoms in the alkylene chain have been optionally replaced with a heteroatom such as —O—, —N—, —S—, —$S(O)_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-aryl, —SO-heteroaryl, —$SO_2$-alkyl, —$SO_2$-aryl, —$SO_2$-heteroaryl, and —NR'R", wherein R' and R" may be the same or different and are chosen from hydrogen, optionally substituted alkyl, cycloalkyl, alkenyl, cycloalkenyl, alkynyl, aryl, heteroaryl and heterocyclic.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

The term "alkenyl" refers to a monoradical of a branched or unbranched unsaturated hydrocarbon group having from 2 to 40 carbon atoms, from 2 to 10 carbon atoms, or from 2 to 6 carbon atoms and having at least 1 site (e.g., from 1-6 sites) of vinyl unsaturation.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

The term "alkynyl" refers to a monoradical of an unsaturated hydrocarbon having from 2 to 40 carbon atoms, from 2 to 20 carbon atoms, or from 2 to 6 carbon atoms and having at least 1 site (e.g., from 1-6 sites) of acetylene (triple bond) unsaturation.

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl, and —$SO_2$-heteroaryl.

The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl, and heterocyclic are as defined herein.

The term "acylamino" or "aminocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl, and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl, and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl, and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl). Exemplary aryls include phenyl, naphthyl and the like. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

The term "aryloxy" refers to the group aryl-O— wherein the aryl group is as defined herein including optionally substituted aryl groups as also defined herein.

The term "amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclic provided that at least one R is not hydrogen.

The term "azido" refers to the group —N$_3$.

The term "carboxyl" refers to —COOH or salts thereof.

The term "carboxyalkyl" or "carboxylalkyl" or "alkoxycarbonyl" refers to the groups "—C(O)O-alkyl", "—C(O)O-substituted alkyl", "—C(O)O-cycloalkyl", "—C(O)O-substituted cycloalkyl", "—C(O)O-alkenyl", "—C(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl alkynyl are as defined herein.

The term "cyano" refers to the group —CN.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl, and the like.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "halo" or "halogen" refers to fluoro, chloro, bromo and iodo.

The term "heteroaryl" refers to an aromatic group of from 1 to 15 carbon atoms and 1 to 4 heteroatoms selected from oxygen, nitrogen and sulfur within at least one ring (if there is more than one ring). Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. Such heteroaralkyl groups are exemplified by pyridylmethyl, pyridylethyl, indolylmethyl, and the like.

The term "heteroaryloxy" refers to the group heteroaryl-O—.

The term "heterocycle" or "heterocyclic" refers to a monoradical saturated or unsaturated group having a single ring or multiple condensed rings, from 1 to 40 carbon atoms and from 1 to 10 hetero atoms, e.g., from 1 to 4 heteroatoms, selected from nitrogen, sulfur, phosphorus, and/or oxygen within the ring. Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

Examples of nitrogen heteroaryls and heterocycles include, but are not limited to, pyrrole, thiophene, furan, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, pyrrolidine, piperidine, piperazine, indoline, morpholine, tetrahydrofuranyl, tetrahydrothiophene, and the like as well as N-alkoxy-nitrogen containing heterocycles.

The term "heterocyclooxy" refers to the group heterocyclic-O—.

The term "heterocyclothio" refers to the group heterocyclic-S—.

The term "heterocyclene" refers to the diradical group formed from a heterocycle, as defined herein, and is exemplified by the groups 2,6-morpholino, 2,5-morpholino and the like.

The term "hydroxyamino" refers to the group —NHOH.

The term "oxo" refers to the group =O.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "thiol" refers to the group —SH.

The term "thioalkoxy" or "alkylthio" refers to the group —S-alkyl.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

The term "thioketo" refers to the group =S.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (e.g., salts having acceptable mammalian safety for a given dosage regime). Such salts can be derived from pharmaceutically acceptable inorganic or organic bases and from pharmaceutically acceptable inorganic or organic acids.

The term "salt thereof" means a compound formed when the hydrogen of an acid is replaced by a cation, such as a metal cation or an organic cation and the like. Where applicable, the salt is a pharmaceutically acceptable salt, although this is not required for salts of intermediate compounds that are not intended for administration to a patient.

The term "solvate" as used herein refers to a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

It will be appreciated that the term "or a salt or solvate or stereoisomer thereof" is intended to include all permutations of salts, solvates and stereoisomers, such as a solvate of a pharmaceutically acceptable salt of a stereoisomer of a compound of formula (I).

The term "therapeutically effective amount" means an amount sufficient to effect treatment when administered to a patient in need of treatment.

The term "treating" or "treatment" as used herein means the treating or treatment of a disease or medical condition in a patient, such as a mammal (particularly a human) that includes: (a) preventing the disease or medical condition from occurring, i.e., prophylactic treatment of a patient; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient.

DETAILED DESCRIPTION

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions comprising these compounds, methods of using these compounds in the treatment of various diseases and disorders, processes for preparing these compounds and intermediates useful in these processes.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and the include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978.

The nomenclature used herein to name the subject compounds is illustrated in the Examples herein. This nomenclature has generally been derived using the commercially-available AutoNom software (MDL, San Leandro, Calif.).

Representative Embodiments

The following substituents and values are intended to provide representative examples of various aspects and embodiments. These representative values are intended to further define and illustrate such aspects and embodiments and are not intended to exclude other embodiments or to limit the scope of this invention. In this regard, the representation that a particular value or substituent is preferred is not intended in any way to exclude other values or substituents from this invention unless specifically indicated.

These compounds may contain one or more chiral centers and therefore, the embodiments are directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions unless otherwise indicated, provided that the desired utility of the composition as a whole is not eliminated by the presence of such other isomers.

In one of its composition aspects, the present embodiments provide a compound of formula (I):

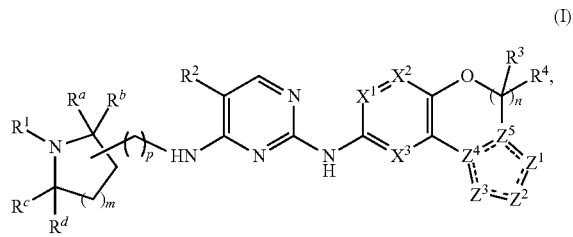

(I)

wherein $R^1$ is selected from hydrogen, alkyl, alkenyl, alkynyl, cycloalkyl, —C(O)OR$^{1a}$, —S(O)R$^{1b}$, and —S(O)$_2$R$^{1c}$; wherein each of R$^{1a}$, R$^{1b}$, and R$^{1c}$ is independently hydrogen, alkyl or phenyl-alkyl;

$R^a$, $R^b$, $R^c$ and $R^d$ independently are selected from hydrogen and alkyl;

m is an integer from one to five;

p is an integer from zero to six;

$R^2$ is selected from acyloxy, hydroxy, thiol, acyl, alkyl, alkoxy, substituted alkyl, substituted alkoxy, amino, substituted amino, aminoacyl, acylamino, azido, carboxyl, carboxylalkyl, cyano, halogen, nitro, aminoacyloxy, oxyacylamino, thioalkoxy, substituted thioalkoxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and trihalomethyl;

$X^1$, $X^2$, and $X^3$ are CR$^5$ or one of $X^1$, $X^2$, and $X^3$ is N and rest are CR$^5$;

$R^5$ is, for each occurrence, selected from hydrogen, halogen, alkyl and substituted alkyl;

$R^3$ and $R^4$ are, for each occurrence, independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^3$ and $R^4$ together with the carbon atom to which they are attached form a carbocyclic or heterocyclic 4 to 8-membered ring;

n is an integer from zero to three;

$Z^1$, $Z^2$, and $Z^3$ are selected from CR$^6$R$^{6a}$, N, O, and S;

$Z^4$ and $Z^5$ are selected from N, C, and CR$^6$;

$R^6$ is selected from hydrogen, halogen, alkyl and substituted alkyl;

$R^{6a}$ is selected from hydrogen, halogen, alkyl and substituted alkyl or is absent to satisfy valence requirements; and the dashed lines represent a single bond or double bond;

or a salt or solvate or stereoisomer thereof.

The groups $Z^1$, $Z^2$, $Z^3$, $Z^4$, and $Z^5$ and the sites of the optional double bonds indicated by the dashed lines in the formulas are selected such that the ring containing these groups satisfies valence requirements. For example, the ring may contain one or two double bonds or no double bonds as indicated by the dashed lines in this ring. If the ring is aromatic, the double bonds are positioned properly and the number of substituents on $Z^1$, $Z^2$, $Z^3$, $Z^4$, and $Z^5$ are such that aromaticity occurs.

$R^1$ can be selected from hydrogen, alkyl, alkenyl, alkynyl, cycloalkyl, —C(O)OR$^{1a}$, —S(O)R$^{1b}$, and —S(O)$_2$R$^{1c}$; wherein each of R$^{1a}$, R$^{1b}$, and R$^{1c}$ is independently hydrogen, alkyl or phenyl-alkyl. In certain instances, $R^1$ is hydrogen, alkyl, or cycloalkyl. In certain instances, $R^1$ is alkenyl or alkynyl. In certain instances, $R^1$ is —C(O)OR$^{1a}$, —S(O)R$^{1b}$, or —S(O)$_2$R$^{1c}$; wherein each of R$^{1a}$, R$^{1b}$, and R$^{1c}$ is independently hydrogen, alkyl or phenyl-alkyl. In certain cases, $R^1$ is selected from hydrogen and alkyl. In one case, $R^1$ is hydrogen. In one case, $R^1$ is alkyl. In one case, $R^1$ is methyl.

$R^a$, $R^b$, $R^c$, and $R^d$ independently are selected from hydrogen and alkyl. In certain cases, at least one or two of $R^a$, $R^b$, $R^c$, and $R^d$ are lower alkyl. In certain instances, $R^a$, $R^b$, $R^c$, and $R^d$ represent lower alkyl groups. In certain instances, $R^a$, $R^b$, $R^c$, and $R^d$ represent methyl. In certain instances, $R^a$, $R^b$, $R^c$, and $R^d$ represent hydrogen.

The value for m can be from one to five. In certain instances, m is an integer from one to three. In one case, m is one or two. In one case, m is one. In one case, m is two.

The value for p can be an integer from zero to six. In certain instances, p is an integer from zero to four or an integer from zero to three. In one case, p is zero or one. In one case, p is zero. In one case, p is one.

$R^2$ can be selected from acyloxy, hydroxy, thiol, acyl, alkyl, alkoxy, substituted alkyl, substituted alkoxy, amino, substituted amino, aminoacyl, acylamino, azido, carboxyl, carboxylalkyl, cyano, halogen, nitro, aminoacyloxy, oxyacylamino, thioalkoxy, substituted thioalkoxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl, and trihalomethyl. In certain instances, $R^2$ is hydroxy, alkyl, substituted alkyl, alkoxy, substituted alkoxy, cyano, halogen, nitro, trihalomethyl, acyloxy, acyl, or acylamino. In certain instances, $R^2$ is thiol, amino, substituted amino, aminoacyl, aminoacyloxy, oxyacylamino, or thioalkoxy, substituted thioalkoxy. In certain instances, $R^2$ is azido, carboxyl, carboxylalkyl, —SO-alkyl, —SO-substituted alkyl, —SO-aryl, —SO-heteroaryl, —$SO_2$-alkyl, —$SO_2$-substituted alkyl, —$SO_2$-aryl, or —$SO_2$-heteroaryl. In one case, $R^2$ is hydroxy, alkyl, alkoxy, cyano, halogen, nitro, or trihalomethyl. In one case, $R^2$ is halogen. In one case, $R^2$ is fluoro. In one case, $R^2$ is hydroxyl. $R^2$ is alkyl.

With continued reference to formula (I), $X^1$, $X^2$, and $X^3$ can be $CR^5$ or one of $X^1$, $X^2$, and $X^3$ can be N and rest are $CR^5$; where $R^5$ for each occurrence independently is selected from hydrogen, halogen, alkyl and substituted alkyl. In certain instances, $X^1$, $X^2$, and $X^3$ is $CR^5$, where $R^5$ for each occurrence is selected from hydrogen, halogen, alkyl and substituted alkyl. In some cases, $X^1$, $X^2$, and $X^3$ is $CR^5$, where $R^5$ for each occurrence is hydrogen, alkyl, or substituted alkyl. In some cases, $X^1$, $X^2$, and $X^3$ is $CR^5$, where $R^5$ for each occurrence is hydrogen, fluoro, alkyl or haloalkyl. In certain instances, $X^1$, $X^2$, and $X^3$ are CH. In certain instances, one of $X^1$, $X^2$, and $X^3$ is N and rest are $CR^5$. In one case, $X^1$ is N. In one case, $X^2$ is N. In one case, $X^3$ is N.

The value for n can be from one to three. In one case, n is one or two. In one case, n is one. In one case, n is two.

$R^3$ and $R^4$ can be, for each occurrence, independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^3$ and $R^4$ together with the carbon atom to which they are attached form a carbocyclic or heterocyclic 4 to 8-membered ring.

In certain instances, $R^3$ and $R^4$ can be, for each occurrence, independently selected from hydrogen, alkyl, substituted alkyl, alkoxy, substituted alkoxy, acyl, acylamino, acyloxy, cyano, halogen, hydroxyl, carboxyl, carboxylalkyl, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl. In certain cases, $R^3$ and $R^4$ are, for each occurrence, independently selected from hydrogen, alkyl, substituted alkyl, alkoxy, substituted alkoxy, cyano, halogen, hydroxyl, and nitro. In certain cases, $R^3$ and $R^4$ are, for each occurrence, independently selected from hydrogen, alkyl, and halogen.

In certain instances, $R^3$ and $R^4$ together with the carbon atom to which they are attached form a carbocyclic or heterocyclic 4 to 8-membered ring. In certain cases, $R^3$ and $R^4$ together with the carbon atom to which they are attached form a carbocyclic or heterocyclic 4 or 5-membered ring. In certain instances, $R^3$ and $R^4$ together with the carbon atom to which they are attached form a carbocyclic or heterocyclic 6-membered ring. In certain instances, $R^3$ and $R^4$ together with the carbon atom to which they are attached form a carbocyclic or heterocyclic 7 or 8-membered ring. In certain cases, the ring is carbocyclic. In certain cases, the ring is heterocyclic, such as a ring comprising O, S or N.

$Z^1$, $Z^2$, and $Z^3$ can be selected from $CR^6$, N, O, and S; where $R^6$ is selected from hydrogen, halogen, alkyl and substituted alkyl; and the dashed lines represent a single bond or double bond. In certain instances, $Z^1$, $Z^2$, and $Z^3$ can be selected from $CR^6$ and N. In certain instances, $Z^1$, $Z^2$, and $Z^3$ can be selected from CH and N. In certain instances, $Z^1$, $Z^2$, and $Z^3$ can be selected from $CR^6$ and O. In certain instances, $Z^1$, $Z^2$, and $Z^3$ can be selected from $CR^6$ and S. In certain cases, $Z^1$, $Z^2$, and $Z^3$ are each N. In certain cases, $Z^1$, $Z^2$, and $Z^3$ are each CH. When $Z^1$, $Z^2$, or $Z^3$ is S or N, these atoms can optionally be substituted with one or more oxygen atoms. For example $Z^1$, $Z^2$, or $Z^3$ independently can be a sulfoxide [S(O) or sulfonyl $S(O)_2$] group. Similarly, $Z^1$, $Z^2$, and $Z^3$ also can represent an N-oxide group, (N→O).

$Z^4$ and $Z^5$ are selected from N, C, and $CR^6$. In certain instances, $Z^4$ is N. In certain instances, $Z^4$ is C. In certain instances, $Z^4$ is $CR^6$. In certain instances, $Z^5$ is N. In certain instances, $Z^5$ is C. In certain instances, $Z^5$ is $CR^6$.

A group of compounds of interest are compounds of formula (I), wherein $X^1$, $X^2$, and $X^3$ are CH; and $R^2$ is fluoro. In certain cases, in formula (I), $X^1$, $X^2$, and $X^3$ are CH; $R^2$ is fluoro; and $R^3$ and $R^4$ are hydrogen, methyl, or fluoro. In certain cases, in formula (I), $X^1$, $X^2$, and $X^3$ are CH; $R^2$ is fluoro; and $Z^1$, $Z^2$, and $Z^3$ are each N. In certain cases, in formula (I), $X^1$, $X^2$, and $X^3$ are CH; $R^2$ is fluoro; and $Z^1$, $Z^2$, and $Z^3$ are each CH.

Another group of compounds of interest are compounds of formula (I), wherein m is 2; and p is zero. In certain cases, in formula (I), m is 2; p is zero; and $R^2$ is fluoro.

Another group of compounds of interest are compounds of formula (I), wherein m is one; and p is one. In certain cases, in formula (I), m is one; p is one; and $R^2$ is fluoro.

Another group of compounds of interest are compounds of formula (I), wherein $X^2$ is N; $X^1$ and $X^3$ are CH; and $R^2$ is fluoro. In certain cases, in formula (I), $X^2$ is N; $X^1$ and $X^3$ are CH; $R^2$ is fluoro; and $R^3$ and $R^4$ are hydrogen, methyl, or fluoro. In certain cases, in formula (I), $X^2$ is N; $X^1$ and $X^3$ are CH; $R^2$ is fluoro; and $Z^1$, $Z^2$, and $Z^3$ are each N. In certain cases, in formula (I), $X^2$ is N; $X^1$ and $X^3$ are CH; $R^2$ is fluoro; and $Z^1$, $Z^2$, and $Z^3$ are each CH.

Another group of compounds of interest are compounds of formula (I), wherein $X^3$ is N; $X^1$ and $X^2$ are CH; and $R^2$ is fluoro. In certain cases, in formula (I), $X^3$ is N; $X^1$ and $X^2$ are CH; $R^2$ is fluoro; and $R^3$ and $R^4$ are hydrogen, methyl, or fluoro. In certain cases, in formula (I), $X^3$ is N; $X^1$ and $X^2$ are CH; $R^2$ is fluoro; and $Z^1$, $Z^2$, and $Z^3$ are each N. In certain cases, in formula (I), $X^3$ is N; $X^1$ and $X^2$ are CH; $R^2$ is fluoro; and $Z^1$, $Z^2$, and $Z^3$ are each CH.

Another group of compounds of interest are compounds of formula (I), wherein n is one; and $R^3$ and $R^4$ are, for each occurrence, independently selected from hydrogen, alkyl, substituted alkyl, alkoxy, substituted alkoxy, cyano, halogen, hydroxyl, and nitro.

Another group of compounds of interest are compounds of formula (I), wherein n is one; and $R^3$ and $R^4$ are, for each occurrence, independently selected from hydrogen, alkyl, and halogen.

Another group of compounds of interest are compounds of formula (I), wherein n is one; and $R^3$ and $R^4$ are the same and are selected from hydrogen, alkyl, and halogen.

Another group of compounds of interest are compounds of formula (I), wherein n is 1; and one of $R^3$ and $R^4$ is hydrogen and the other is selected from alkyl and halogen. In certain cases, the compound is enantiomerically enriched (R)-configuration or (S)-configuration at the carbon comprising $R^3$ and $R^4$. In certain cases, the compound is racemic.

Another group of compounds of interest are compounds of formula (I), wherein n is 2; and $R^3$ and $R^4$ are, for each occurrence, independently selected from hydrogen, alkyl, substituted alkyl, alkoxy, substituted alkoxy, cyano, halogen, hydroxyl, and nitro.

Another group of compounds of interest are compounds of formula (I), wherein n is 2; and $R^3$ and $R^4$ are, for each occurrence, independently selected from hydrogen, alkyl, and halogen.

Another group of compounds of interest are compounds of formula (I), wherein n is 2; and $R^3$ and $R^4$ on the same carbon are the same and are selected from hydrogen, alkyl, and halogen.

Another group of compounds of interest are compounds of formula (I), wherein n is 2; and on a given carbon comprising $R^3$ and $R^4$, one of $R^3$ and $R^4$ is hydrogen and the other is selected from alkyl and halogen. In certain cases, the compound is enantiomerically enriched. In certain cases, the compound is racemic.

Certain compounds of interest have formula (I) wherein $R^a$, $R^b$, $R^c$ and $R^d$ represent lower alkyl groups. Particular examples of such compounds include those wherein $R^a$, $R^b$, $R^c$ and $R^d$ are methyl groups and have formula (II):

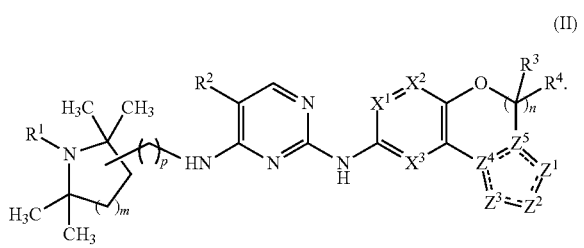

(II)

A particular group of compounds of interest are compounds of formula (I), wherein $X^1$, $X^2$, and $X^3$ are each CH. These compounds have the following formula (III):

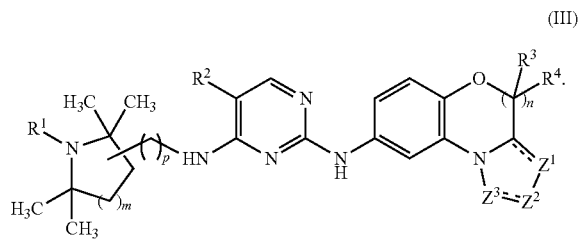

(III)

A particular group of compounds of interest are compounds of formula (I), wherein $X^1$, $X^2$, and $X^3$ are each CH; and m is 2. These compounds have the following formula (IV):

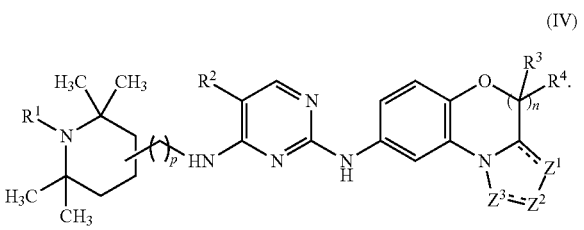

(IV)

A particular group of compounds of interest are compounds of formula (I), wherein $X^1$, $X^2$, and $X^3$ are each CH; and m is one. These compounds have the following formula (V):

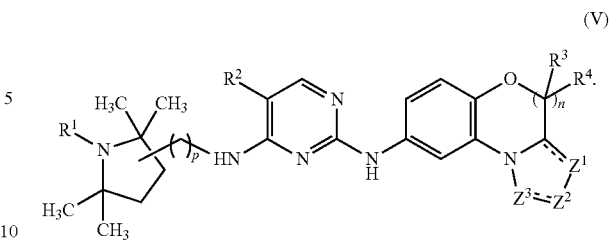

(V)

A particular group of compounds of interest are compounds of formula (I), wherein $X^1$, $X^2$, and $X^3$ are each CH; n is 2; and one set of $R^3$ and $R^4$ is hydrogen. These compounds have the following formula (VI):

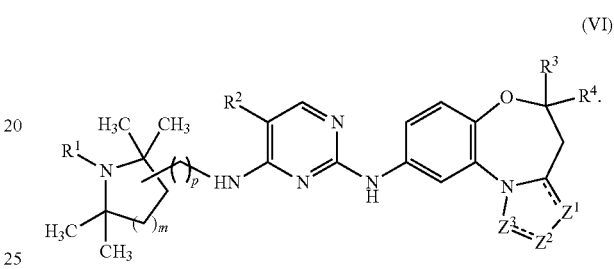

(VI)

A particular group of compounds of interest are compounds of formula (I), wherein $X^2$ is N and $X^1$ and $X^3$ are each CH. These compounds have the following formula (VII):

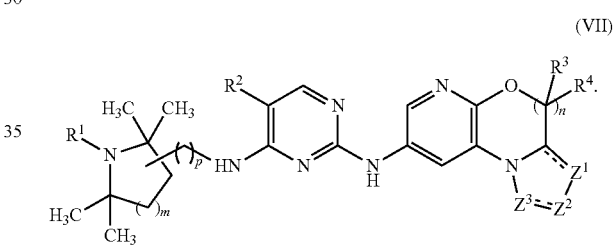

(VII)

A particular group of compounds of interest are compounds of formula (I), wherein $X^3$ is N and $X^1$ and $X^2$ are each CH. These compounds have the following formula (VIII):

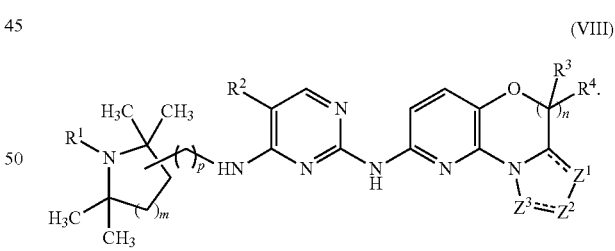

(VIII)

An additional group of compounds of interest have formula (I), wherein $Z^4$ is C and $Z^5$ is N. Such compounds have the following formula (IX):

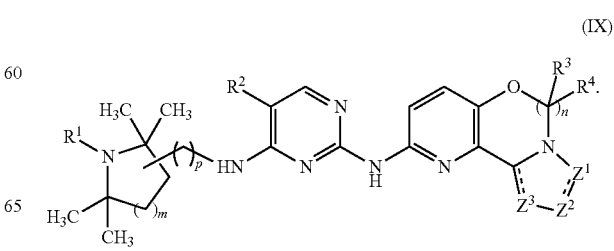

(IX)

Particular compounds of interest are shown in the following tables.
TABLE 1
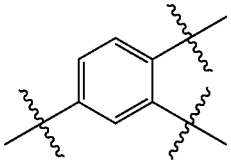 [SMILES: *c1ccc(*)c(*)c1]
| Compound | R¹ | R² | R³ | R⁴ | Ring 1 | Ring 2 |
|---|---|---|---|---|---|---|
| 1-1 | —H | —F | —H | —H | 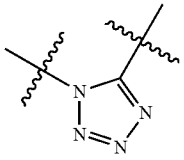 [SMILES: *c1nnnn1*] | 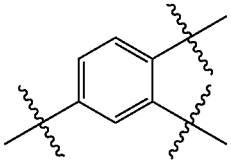 [SMILES: *c1ccc(*)c(*)c1] |
| 1-2 | —CH₃ | —F | —H | —H | 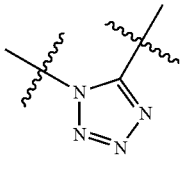 [SMILES: *c1nnnn1*] | 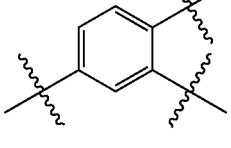 |
| 1-3 | —H | —F | —H | —H | 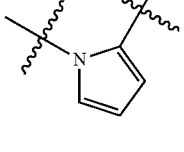 | 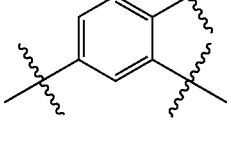 |
| 1-4 | —CH₃ | —F | —H | —H | 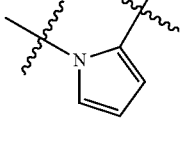 | 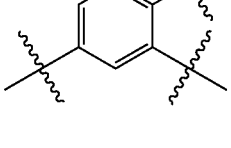 |
| 1-5 | —H | —F | —F | —F | 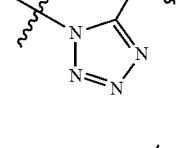 | 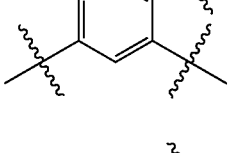 |
| 1-6 | —CH₃ | —F | —F | —F | 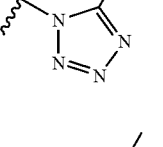 | 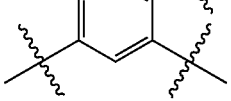 |
| 1-7 | —H | —F | —CH₃ | —CH₃ | 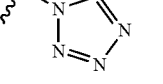 | |

TABLE 1-continued

| Compound | R¹ | R² | R³ | R⁴ | Ring 1 | Ring 2 |
|---|---|---|---|---|---|---|
| 1-8 | —CH₃ | —F | —CH₃ | —CH₃ | 1,2,4-trisubstituted benzene | 1,5-disubstituted tetrazole (N1) |
| 1-9 | —H | —F | —CH₃ | —CH₃ | 1,2,4-trisubstituted benzene | 1,5-disubstituted tetrazole (N1) |
| 1-10 | —CH₃ | —F | —CH₃ | —CH₃ | 1,2,4-trisubstituted benzene | 1,5-disubstituted tetrazole (N1) |
| 1-11 | —H | —F | cyclobutylidene (spiro) | | 1,2,4-trisubstituted benzene | 1,5-disubstituted tetrazole (N1) |
| 1-12 | —CH₃ | —F | cyclobutylidene (spiro) | | 1,2,4-trisubstituted benzene | 1,5-disubstituted tetrazole (N1) |
| 1-13 | —H | —F | cyclohexylidene (spiro) | | 1,2,4-trisubstituted benzene | 1,5-disubstituted tetrazole (N1) |
| 1-14 | —CH₃ | —F | cyclohexylidene (spiro) | | 1,2,4-trisubstituted benzene | 1,5-disubstituted tetrazole (N1) |

TABLE 1-continued

| Compound | R¹ | R² | R³ | R⁴ | Ring 1 | Ring 2 |
|---|---|---|---|---|---|---|
| 1-15 | —H | —F | —CH₃ | —H | phenyl | tetrazole |
| 1-16 | —CH₃ | —F | —CH₃ | —H | phenyl | tetrazole |
| 1-17 | —H | —F | (R,S)-CH₃ | —H | phenyl | tetrazole |
| 1-18 | —CH₃ | —F | (R,S)-CH₃ | —H | phenyl | tetrazole |
| 1-19 | —H | —F | (R)-CH₃ | —H | phenyl | tetrazole |
| 1-20 | —CH₃ | —F | (R)-CH₃ | —H | phenyl | tetrazole |
| 1-21 | —H | —F | (S)-CH₃ | —H | phenyl | tetrazole |

TABLE 1-continued

| Compound | R¹ | R² | R³ | R⁴ | Ring 1 | Ring 2 |
|---|---|---|---|---|---|---|
| 1-22 | —CH₃ | —F | (S)-CH₃ | —H | benzene (1,2,4-trisubstituted) | tetrazole (N-linked) |
| 1-23 | —H | —F | —CH₃ | —CH₃ | pyridine | tetrazole (N-linked) |
| 1-24 | —CH₃ | —F | —CH₃ | —CH₃ | pyridine | tetrazole (N-linked) |
| 1-25 | —H | —F | —CH₃ | —CH₃ | pyridine | tetrazole (N-linked) |
| 1-26 | —CH₃ | —F | —CH₃ | —CH₃ | pyridine | tetrazole (N-linked) |

TABLE 2

| Compound | R¹ | R² | R³ | R⁴ | Ring 1 | Ring 2 | * center |
|---|---|---|---|---|---|---|---|
| 2-1 | —H | —F | —H | —H | benzene | tetrazole | |
| 2-2 | —CH₃ | —F | —H | —H | benzene | tetrazole | |
| 2-3 | —H | —F | —H | —H | benzene | pyrrole | |
| 2-4 | —CH₃ | —F | —H | —H | benzene | pyrrole | |
| 2-5 | —H | —F | —F | —F | benzene | tetrazole | |
| 2-6 | —CH₃ | —F | —F | —F | benzene | tetrazole | |
| 2-7 | —H | —F | —CH₃ | —CH₃ | benzene | tetrazole | * center is (S) (+) |

TABLE 2-continued
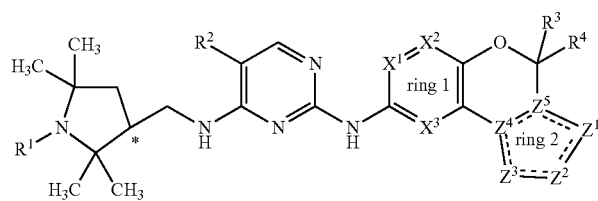
where * indicates a chiral center
| Compound | R¹ | R² | R³ | R⁴ | Ring 1 | Ring 2 | * center |
|---|---|---|---|---|---|---|---|
| 2-8 | —H | —F | —CH₃ | —CH₃ | benzene | tetrazole | * center is (R) (−) |
| 2-9 | —CH₃ | —F | —CH₃ | —CH₃ | benzene | tetrazole | * center is (S) (+) |
| 2-10 | —CH₃ | —F | —CH₃ | —CH₃ | benzene | tetrazole | * center is (R) (−) |
| 2-11 | —H | —F | —CH₃ | —CH₃ | benzene | tetrazole | |
| 2-12 | —CH₃ | —F | —CH₃ | —CH₃ | benzene | tetrazole | |
| 2-13 | —H | —F | —CH₃ | —CH₃ | benzene | tetrazole | |
| 2-14 | —CH₃ | —F | —CH₃ | —CH₃ | benzene | tetrazole | |

TABLE 2-continued

| Compound | R¹ | R² | R³ | R⁴ | Ring 1 | Ring 2 | * center |
|---|---|---|---|---|---|---|---|
| 2-15 | —H | —F | cyclobutyl (spiro) | | phenyl | tetrazole | |
| 2-16 | —CH₃ | —F | cyclobutyl (spiro) | | phenyl | tetrazole | |
| 2-17 | —H | —F | cyclohexyl (spiro) | | phenyl | tetrazole | |
| 2-18 | —CH₃ | —F | cyclohexyl (spiro) | | phenyl | tetrazole | |
| 2-19 | —H | —F | —CH₃ | —H | phenyl | tetrazole | |
| 2-20 | —CH₃ | —F | —CH₃ | —H | phenyl | tetrazole | |
| 2-21 | —H | —F | (R,S)-CH₃ | —H | phenyl | tetrazole | |

TABLE 2-continued
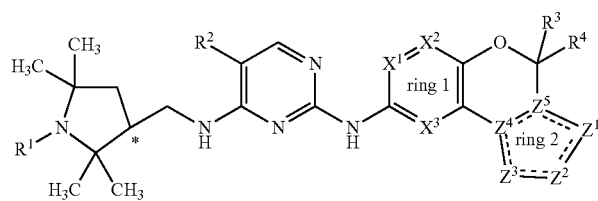
where * indicates a chiral center
| Compound | R¹ | R² | R³ | R⁴ | Ring 1 | Ring 2 | * center |
|---|---|---|---|---|---|---|---|
| 2-22 | —CH₃ | —F | (R,S)-CH₃ | —H | benzene | tetrazole | |
| 2-23 | —H | —F | (R)-CH₃ | —H | benzene | tetrazole | |
| 2-24 | —CH₃ | —F | (R)-CH₃ | —H | benzene | tetrazole | |
| 2-25 | —H | —F | (S)-CH₃ | —H | benzene | tetrazole | |
| 2-26 | —CH₃ | —F | (S)-CH₃ | —H | benzene | tetrazole | |
| 2-27 | —H | —F | —CH₃ | —CH₃ | pyridine | tetrazole | |
| 2-28 | —CH₃ | —F | —CH₃ | —CH₃ | pyridine | tetrazole | |

TABLE 2-continued

| Compound | R¹ | R² | R³ | R⁴ | Ring 1 | Ring 2 | * center |
|---|---|---|---|---|---|---|---|
| 2-29 | —H | —F | —CH₃ | —CH₃ | pyridine (2,3,6-linked) | tetrazole (N,C-linked) | |
| 2-30 | —CH₃ | —F | —CH₃ | —CH₃ | pyridine (2,3,6-linked) | tetrazole (N,C-linked) | | where * indicates a chiral center

TABLE 3

| Compound | R¹ | R² | R³ | R⁴ | Ring 1 | Ring 2 |
|---|---|---|---|---|---|---|
| 3-1 | —H | —F | —CH₃ | —CH₃ | benzene (1,2,4-linked) | tetrazole (N,C-linked) |
| 3-2 | —CH₃ | —F | —CH₃ | —CH₃ | benzene (1,2,4-linked) | tetrazole (N,C-linked) |

Particular compounds of interest, and salts or solvates or stereoisomers thereof, include:

N2-(4H-benzo[b]tetrazolo[1,5-d][1,4]oxazin-8-yl)-5-fluoro-N4-(2,2,6,6-tetramethylpiperidin-4-yl)pyrimidine-2,4-diamine;

N2-(4H-benzo[b]tetrazolo[1,5-d][1,4]oxazin-8-yl)-5-fluoro-N4-(1,2,2,6,6-pentamethylpiperidin-4-yl)pyrimidine-2,4-diamine;

N2-(4H-benzo[b]pyrrolo[1,2-d][1,4]oxazin-8-yl)-5-fluoro-N4-(2,2,6,6-tetramethylpiperidin-4-yl)pyrimidine-2,4-diamine;

N2-(4H-benzo[b]pyrrolo[1,2-d][1,4]oxazin-8-yl)-5-fluoro-N4-(1,2,2,6,6-pentamethylpiperidin-4-yl)pyrimidine-2,4-diamine;

N2-(4,4-difluoro-4H-benzo[b]tetrazolo[1,5-d][1,4]oxazin-8-yl)-5-fluoro-N4-(2,2,6,6-tetramethylpiperidin-4-yl)pyrimidine-2,4-diamine;

N2-(4,4-difluoro-4H-benzo[b]tetrazolo[1,5-d][1,4]oxazin-8-yl)-5-fluoro-N4-(1,2,2,6,6-pentamethylpiperidin-4-yl)pyrimidine-2,4-diamine;

N2-(4,4-dimethyl-4H-benzo[b]tetrazolo[1,5-d][1,4]oxazin-8-yl)-5-fluoro-N4-(1,2,2,6,6-pentamethylpiperidin-4-yl)pyrimidine-2,4-diamine;

N2-(4,4-dimethyl-4H-benzo[b]tetrazolo[1,5-d][1,4]oxazin-8-yl)-5-fluoro-N4-(2,2,6,6-tetramethylpiperidin-4-yl)pyrimidine-2,4-diamine;

N2-(5,5-dimethyl-5H-benzo[e]tetrazolo[1,5-c][1,3]oxazin-9-yl)-5-fluoro-N4-(2,2,6,6-tetramethylpiperidin-4-yl)pyrimidine-2,4-diamine;

N2-(5,5-dimethyl-5H-benzo[e]tetrazolo[1,5-c][1,3]oxazin-9-yl)-5-fluoro-N4-(1,2,2,6,6-pentamethylpiperidin-4-yl)pyrimidine-2,4-diamine;

N2-(8,9-dihydrospiro[benzo[b]tetrazolo[1,5-d][1,4]oxazine-4,1'-cyclobutane]-8-yl)-5-fluoro-N4-(2,2,6,6-tetramethylpiperidin-4-yl)pyrimidine-2,4-diamine;

N2-(8,9-dihydrospiro[benzo[b]tetrazolo[1,5-d][1,4]oxazine-4,1'-cyclobutane]-8-yl)-5-fluoro-N4-(1,2,2,6,6-pentamethylpiperidin-4-yl)pyrimidine-2,4-diamine;

5-fluoro-N2-(4-methyl-8,9-dihydro-4H-benzo[b]tetrazolo[1,5-d][1,4]oxazin-8-yl)-N4-(2,2,6,6-tetramethylpiperidin-4-yl)pyrimidine-2,4-diamine;

5-fluoro-N2-(4-methyl-8,9-dihydro-4H-benzo[b]tetrazolo[1,5-d][1,4]oxazin-8-yl)-N4-(1,2,2,6,6-pentamethylpiperidin-4-yl)pyrimidine-2,4-diamine;

N2-(4H-benzo[b]tetrazolo[1,5-d][1,4]oxazin-8-yl)-5-fluoro-N4-((1,2,2,5,5-pentamethylpyrrolidin-3-yl)methyl)pyrimidine-2,4-diamine;

N2-(4H-benzo[b]tetrazolo[1,5-d][1,4]oxazin-8-yl)-5-fluoro-N4-((2,2,5,5-tetramethylpyrrolidin-3-yl)methyl)pyrimidine-2,4-diamine;

N2-(4,4-dimethyl-4H-benzo[b]tetrazolo[1,5-d][1,4]oxazin-8-yl)-5-fluoro-N4-((1,2,2,5,5-pentamethylpyrrolidin-3-yl)methyl)pyrimidine-2,4-diamine;

N2-(4,4-dimethyl-4H-benzo[b]tetrazolo[1,5-d][1,4]oxazin-8-yl)-5-fluoro-N4-((2,2,5,5-tetramethylpyrrolidin-3-yl)methyl)pyrimidine-2,4-diamine;

N2-(4,4-dimethyl-4H-benzo[b]tetrazolo[1,5-d][1,4]oxazin-8-yl)-5-fluoro-N4-(((3S)-2,2,5-trimethylpyrrolidin-3-yl)methyl)pyrimidine-2,4-diamine; and N2-(4,4-dimethyl-4H-benzo[b]tetrazolo[1,5-d][1,4]oxazin-8-yl)-5-fluoro-N4-(((3R)-2,2,5-trimethylpyrrolidin-3-yl)methyl)pyrimidine-2,4-diamine.

The present disclosure also provides pharmaceutical compositions comprising a pharmaceutically acceptable carrier and a therapeutically effective amount of a compound of formula (I) or a pharmaceutically acceptable salt or solvate or stereoisomer thereof.

A disclosed compound can be administered alone, as the sole active pharmaceutical agent, or in combination with one or more additional compounds of formula (I) or in conjunction with other agents. When administered as a combination, the therapeutic agents can be formulated as separate compositions that are administered simultaneously or at different times, or the therapeutic agents can be administered together as a single composition combining two or more therapeutic agents. Thus, the pharmaceutical compositions disclosed herein containing a compound of formula (I) optionally contain other therapeutic agents. Accordingly, certain embodiments are directed to such pharmaceutical composition, wherein the composition further comprises a therapeutically effective amount of an agent selected as is known to those of skill in the art.

The subject compounds can inhibit a protein kinase C activity. Accordingly, the compounds are useful for treating a disease or disorder that is mediated through the activity of a PKC activity in a subject. Also, the compounds are useful for treating a disease or disorder that is associated with the activation of T-cells in a subject.

The present disclosure provides a method of treating an inflammatory disease in a subject, the method comprising administering to the subject with a compound of formula (I) or a salt or solvate or stereoisomer thereof.

The present disclosure also provides a method of treating an autoimmune disease in a subject, the method comprising administering to the subject with a compound of formula (I) or a salt or solvate or stereoisomer thereof.

The present disclosure also provides a method of treating an ocular disease or disorder involving inflammatory and/or neovascular events.

The present disclosure also provides a method of treating diseases or conditions of interest including, but are not limited to, atherosclerosis, vascular occlusion due to vascular injury, angioplasty, restenosis, obesity, syndrome X, impaired glucose tolerance, polycystic ovary syndrome, hypertension, heart failure, chronic obstructive pulmonary disease, CNS diseases, Alzheimer disease, amyotrophic lateral sclerosis, cancer, infectious disease, AIDS, septic shock, adult respiratory distress syndrome, ischemia/reperfusion injury, myocardial infarction, stroke, gut ischemia, renal failure, hemorrhage shock, and traumatic shock, and traumatic brain injury.

The present disclosure also provides a method of treating diseases or conditions of interest including, but are not limited to, T-cell mediated acute or chronic inflammatory diseases or disorders or autoimmune diseases, rheumatoid arthritis, osteoarthritis, systemic lupus erythematosus, Hashimoto's thyroidis, multiple sclerosis, myasthenia gravis, diabetes type I or II and the disorders associated therewith, transplant rejection, graft versus host disease, respiratory diseases, asthma, inflammatory lung injury, inflammatory liver injury, inflammatory glomerular injury, cutaneous manifestations of immunologically-mediated disorders or illnesses, inflammatory and hyperproliferative skin diseases, psoriasis, atopic dermatitis, allergic contact dermatitis, irritant contact dermatitis and further eczematous dermatitises, seborrhoeic dermatitis, inflammatory eye diseases, Sjoegren's syndrome, keratoconjunctivitis, uveitis, inflammatory bowel disease, Crohn's disease or ulcerative colitis, Guillain-Barre syndrome, and allergies.

The subject compounds can be used for treating a cell proliferative disorder. The present disclosure also provides a method of treating diseases or conditions of interest including, but are not limited to, hematopoietic neoplasm, lymphoid neoplasm, T cell neoplasm, T lymphoblastic leukemia, B cell neoplasm, B-lymphoblastic leukemia, Burkitt's lymphoma, myeloid neoplasm, myeloproferative disease, chronic myelogenous leukemia (CML), myelodysplastic disease, chronic myelomonocytic leukemia, myelodysplastic syndrome, and acute myeloid leukemia.

The subject compounds can be used in combination with a prodrug, or a salt thereof, of a Syk kinase inhibitory compound. A Syk kinase inhibitory compound can have the formula:

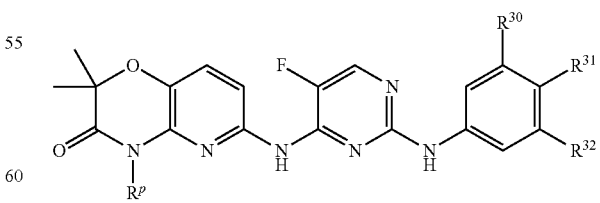

wherein
each $R^{30}$, $R^{31}$ and $R^{32}$ is independently selected from hydrogen, lower alkyl, lower alkenyl, lower alkynyl, (C6-C14) aryl, phenyl, 5-14 membered heteroaryl, (C7-C20) arylalkyl, benzyl, 7-20 membered heteroarylalkyl, —OR, chloro, fluoro, bromo, cyano, nitro, —C(O)R, —C(O)OR, —NRR, —S(O)$_2$NRR, —C(O)NRR, —N(R)S(O)$_2$R and —NC(O)OR, where each R is independently selected from hydrogen and lower alkyl; and R$^p$ is selected from —CH$_2$—O—P(O)(OH)$_2$, —CH$_2$CH$_2$—O—P(O)(OH)$_2$, —CH$_2$OH.

In combination with a prodrug, or a salt thereof, of a Syk kinase inhibitory compound, the composition can be used for treating a cell proliferative disorder. The present disclosure also provides a method of treating diseases or conditions of interest including, but are not limited to, hematopoietic neoplasm, lymphoid neoplasm, T cell neoplasm, T lymphoblastic leukemia, B cell neoplasm, B-lymphoblastic leukemia, Burkitt's lymphoma, myeloid neoplasm, myeloproferative disease, chronic myelogenous leukemia (CML), myelodysplastic disease, chronic myelomonocytic leukemia, myelodysplastic syndrome, and acute myeloid leukemia.

Since subject compounds possess PKC inhibitory properties, such compounds are also useful as research tools. Accordingly, the disclosure also provides for a method for using a compound of formula (I) or a salt or solvate or stereoisomer thereof as a research tool for studying a biological system or sample, or for discovering new chemical compounds having PKC inhibitory properties.

The embodiments are also directed to processes and novel intermediates useful for preparing compounds of formula (I) or a salt or solvate or stereoisomer thereof. Accordingly, the present disclosure provides a process of preparing a compound of formula (I), the process comprising:

contacting a compound of formula:

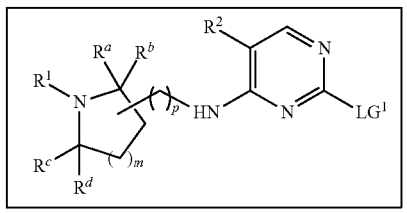

with a compound of

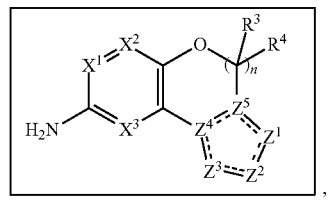

formula wherein LG$^1$ is a leaving group.

In one embodiment, the above process further comprises the step of forming a salt of a compound of formula (I). Embodiments are directed to the other processes described herein; and to the product prepared by any of the processes described herein.

The embodiments are also directed to a compound of formula (I) or a salt or solvate or stereoisomer thereof, for use in therapy or as a medicament.

Additionally, the embodiments are directed to the use of a compound of formula (I) or a salt or solvate or stereoisomer thereof, for the manufacture of a medicament; especially for the manufacture of a medicament for the inhibition of protein kinase C (PKC) activity. The embodiments are also directed to the use of a compound of formula (I) or a salt or solvate or stereoisomer thereof for the manufacture of a medicament for the treatment of a disease or disorder mediated or sustained through the activity of PKC activity. The embodiments are also directed to the use of a compound of formula (I) or a salt or solvate or stereoisomer thereof for the manufacture of a medicament for the treatment of a disease or disorder associated with the activation of T-cells. Diseases or conditions of interest include, but are not limited to, an inflammatory disease, an immunological disorder, an autoimmune disease, an ocular disease or disorder involving inflammatory and/or neovascular events, organ and bone marrow transplant rejection, acute or chronic inflammation, allergies, contact dermatitis, psoriasis, rheumatoid arthritis, multiple sclerosis, type I diabetes, type II diabetes, inflammatory bowel disease, Guillain-Barre syndrome, Crohn's disease, ulcerative colitis, graft versus host disease, and lupus erythematosus.

The embodiments are also directed to the use of a compound of formula (I) or a salt or solvate or stereoisomer thereof for the manufacture of a medicament for the treatment of a cell proliferative disorder. Diseases or conditions of interest include, but are not limited to, hematopoietic neoplasm, lymphoid neoplasm, T cell neoplasm, T lymphoblastic leukemia, B cell neoplasm, B-lymphoblastic leukemia, Burkitt's lymphoma, myeloid neoplasm, myeloproferative disease, chronic myelogenous leukemia (CML), myelodysplastic disease, chronic myelomonocytic leukemia, myelodysplastic syndrome, acute myeloid leukemia.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

A representative synthesis for compounds of formula (I) is shown in Scheme 1.

Scheme 1

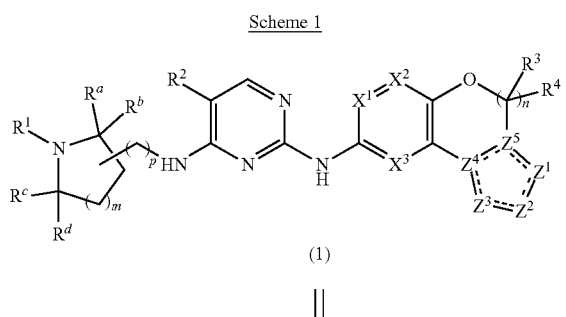

(1)

⇓

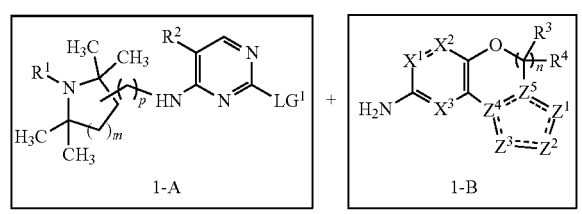

In Scheme 1, Compound 1-A and Compound 1-B react to form Compound I. The compounds react through a nucleophilic aromatic substitution reaction with the amino group of Compound 1-B and the leaving group ($LG^1$) of Compound 1-A. Examples of suitable leaving groups include, but are not limited to, halogen, mesylate, tosylate, and triflate. The nucleophilic reaction can be run neatly or with a suitable solvent. The nucleophilic reaction can be run at various temperatures, including with cooling, at room temperature, or with heating. One skilled in the art would be able to determine suitable reaction conditions according to the specific reactants.

Representative compounds of formula 1-A are shown in Scheme 2. In Scheme 2, Compound 2-A is an embodiment in which m is two, p is zero and $R^a$, $R^b$, $R^c$ and $R^d$ each are methyl. Compound 2-B is an embodiment in which m is one, p is one and $R^a$, $R^b$, $R^c$ and $R^d$ each are methyl. Compound 2-C is an embodiment wherein m is two, p is zero, $R^a$ and $R^c$ are methyl and $R^b$ and $R^d$ are hydrogen.

Scheme 2

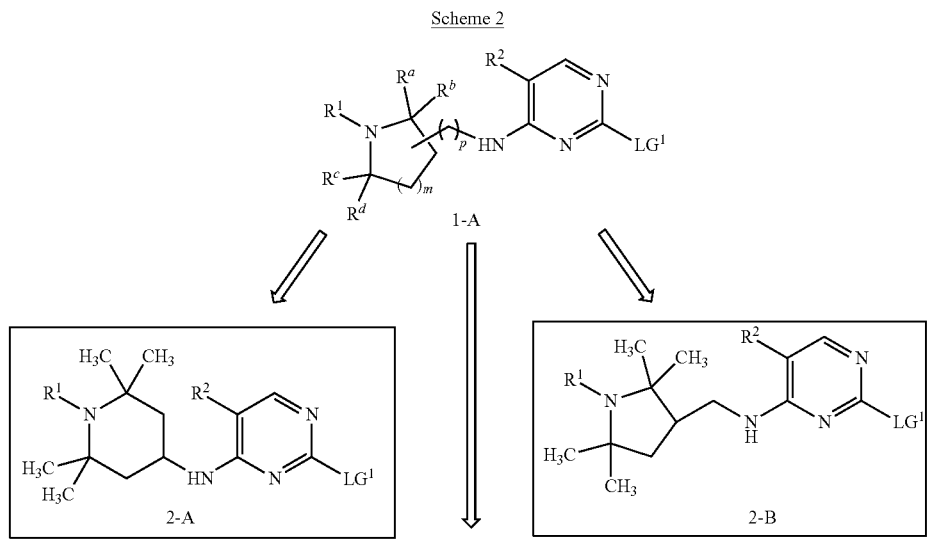

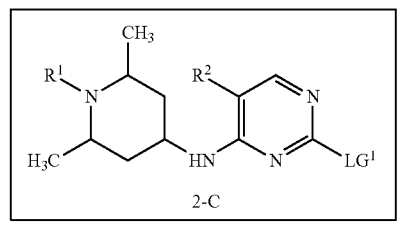

Compounds 2-A, 2-B and 2-C can be synthesized via a variety of different synthetic routes using commercially available starting materials and/or starting materials prepared by conventional synthetic methods. Suitable exemplary methods that may be routinely adapted to synthesize the compounds are found in Section F of U.S. Patent Publication No. 20080306099, the disclosure of which is incorporated herein by reference.

Adapted from Scheme 1 of U.S. Patent Publication No. 20080306099, Compounds 2-A, 2-B and 2-C can be synthesized from substituted or unsubstituted uracils as illustrated in Scheme 3.

078-8; CAS Registry 66-22-8); 5-bromouracil (Aldrich #85, 247-3; CAS Registry 51-20-7; 5-fluorouracil (Aldrich #85, 847-1; CAS Registry 51-21-8); 5-iodouracil (Aldrich #85, 785-8; CAS Registry 696-07-1); 5-nitrouracil (Aldrich #85, 276-7; CAS Registry 611-08-5); 5-(trifluoromethyl)-uracil (Aldrich #22, 327-1; CAS Registry 54-20-6). Additional 5-substituted uracils are available from General Intermediates of Canada, Inc., Edmonton, Calif. and/or Interchim, Cedex, France, or may be prepared using standard techniques.

A representative synthesis for Compounds 2-B is shown in Scheme 4.

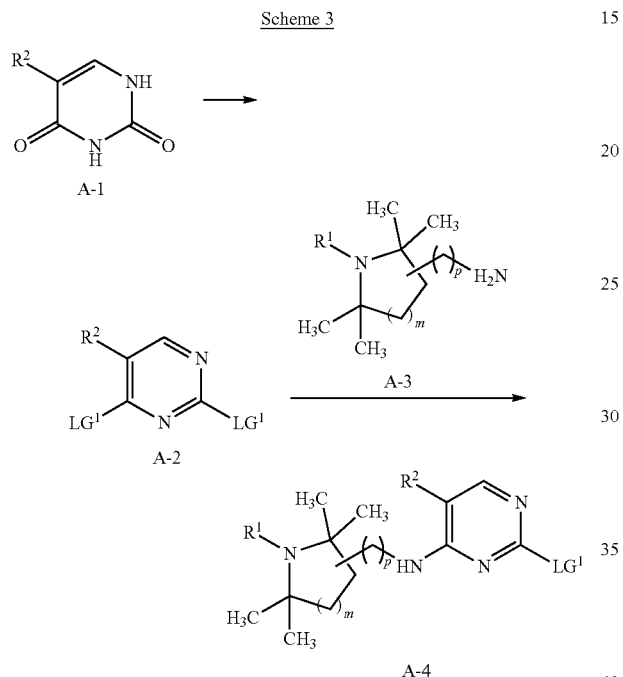

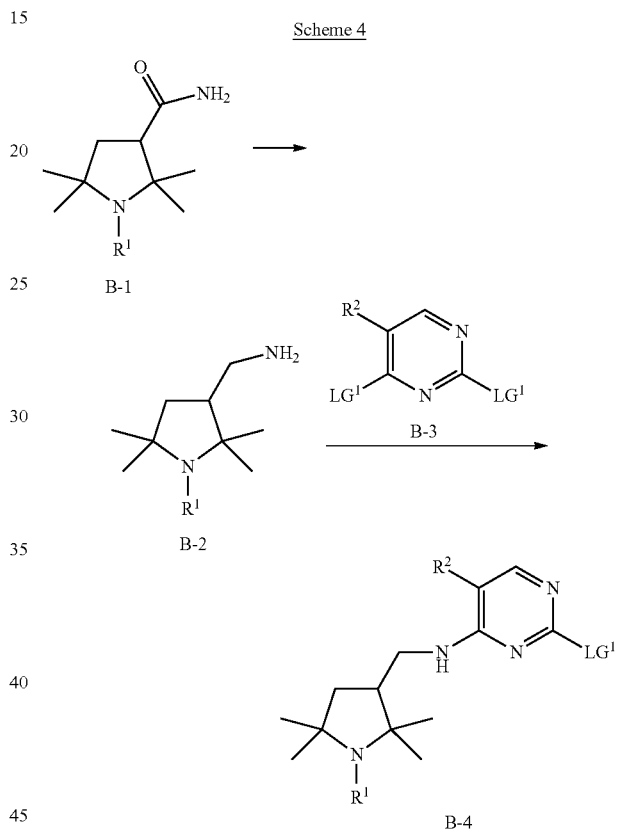

In Scheme 3, $R^1$, $R^2$, $LG^1$, m, and p are as defined herein. According to Scheme 3, uracil A-1 is dihalogenated at the 2- and 4-positions using a standard halogenating agent such as $POCl_3$ (or other standard halogenating agent) under standard conditions to yield 2,4-dichloropyrimidine A-2. Depending upon the $R^2$ substituent in pyrimidinediamine A-2, the leaving group at the C4 position is more reactive towards nucleophiles than the leaving group at the C2 position. This differential reactivity can be exploited to synthesize 2,4-pyrimidinediamines with different substituents at these positions by first reacting 2,4-dichloropyrimidine A-2 with one equivalent of amine A-3, yielding 4N-substituted-2-chloro-4-pyrimidineamine A-4. Further reaction of pyrimidineamine A-4 with a second amine nucleophile can yield a 2,4-pyrimidinediamine derivative with different substituents at the C2 and C4 positions. With continued reference to Scheme 3, A-3 compounds wherein m is two, p is zero, $R^a$ and $R^c$ are methyl and $R^b$ and $R^d$ are hydrogen are prepared as is known to those of skill in the art and according to the procedures provided by Langlois et al. Eur. J. Med. Chem. 1993, 28, 869-880.

The uracil A-1 starting materials may be purchased from commercial sources or prepared using standard techniques of organic chemistry. Commercially available uracils that can be used as starting materials in Scheme 3 include, by way of example and not limitation, uracil (Aldrich #13, In Scheme 4, $R^1$, $R^2$, and $LG^1$ are as defined herein. According to Scheme 4, the amide of Compound B-1 is reduced. The reduction reaction can be carried out in an ethereal solvent, for example ether or tetrahydrofuran, using lithium aluminium hydride or diborane as reducing agents. Then, Compounds B-2 and B-3 react in a nucleophilic reaction in which the amino group displaces one of the leaving groups. The selectivity of the leaving groups is explained herein. The nucleophilic reaction can be run neatly or with a suitable solvent. The nucleophilic reaction can be run at various temperatures, including with cooling, at room temperature, or with heating. One skilled in the art would be able to determine suitable reaction conditions according to the specific reactants.

With continued reference to Scheme 4, amine B-2 has a chiral center. Accordingly, B-2 in the present compounds was used both in racemic and enantiomerically enriched forms. Optically active amine B-2 was prepared as illustrated in Scheme 5 and was incorporated into exemplary compounds as set forth in Scheme 4.

Scheme 5

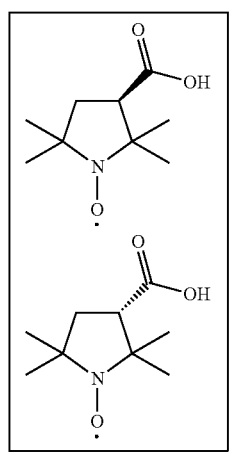

1. ClCO₂Et, NMM, 0° C.
2. NH₃/THF

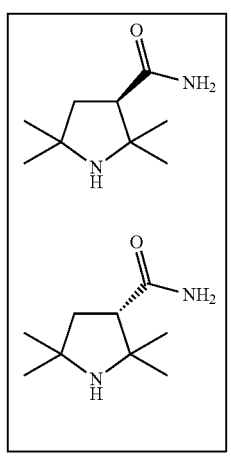

1M LiAlH₄ in THF, Reflux

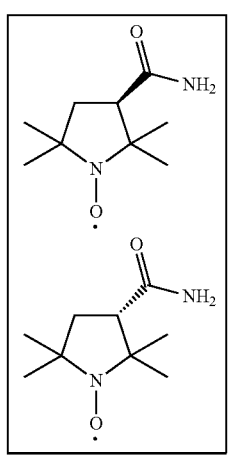

Zn/HCl, 100° C., 1 h.

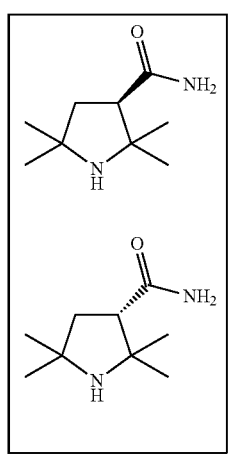

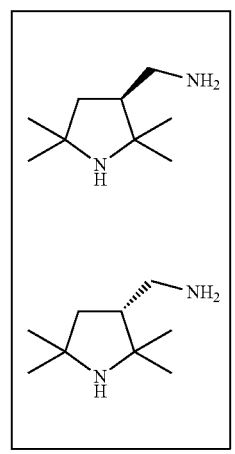

Representative compounds of formula 1-B are shown in Scheme 6. In Scheme 6, Compound 3-A is an embodiment in which $X^1$, $X^2$, and $X^3$ are CH; n is one; $R^3$ and $R^4$ are hydrogen; and $Z^1$, $Z^2$, and $Z^3$ are CH. Compound 3-B is an embodiment in which $X^1$, $X^2$, and $X^3$ are CH; n is one; $R^3$ and $R^4$ are hydrogen; and $Z^1$, $Z^2$, and $Z^3$ are N.

Scheme 6

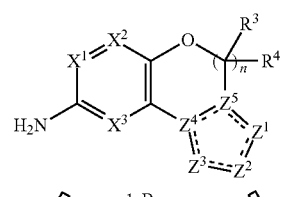

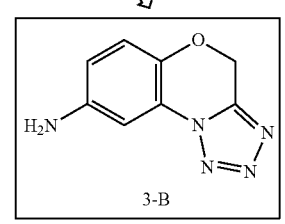

A representative synthesis for Compound 3-A is shown in Scheme 7.

Scheme 7

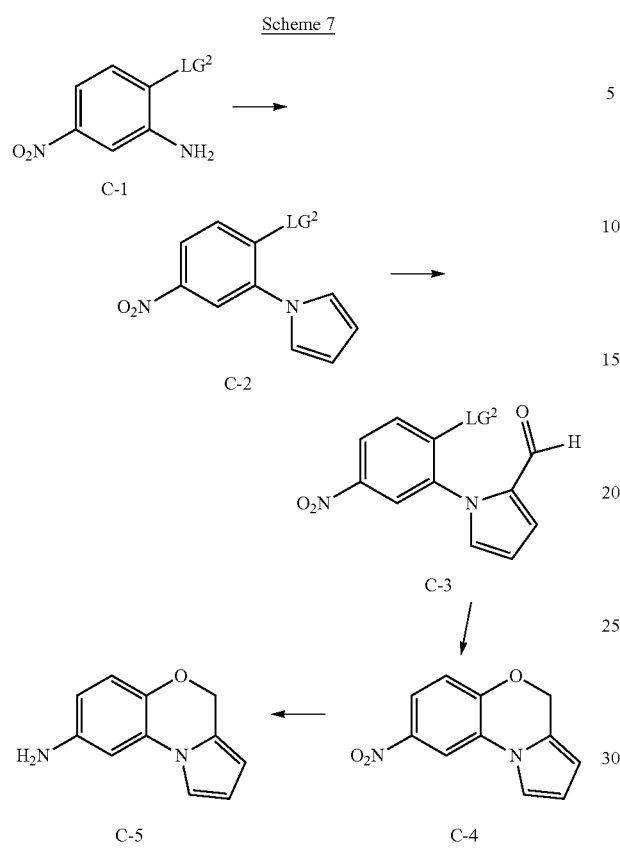

Scheme 8

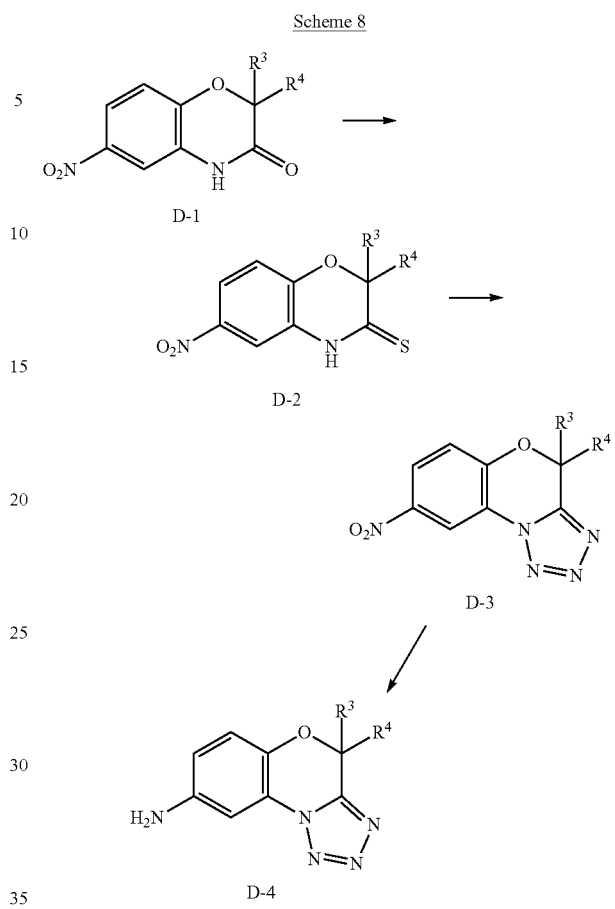

In Scheme 7, $LG^2$ is a leaving group. Examples of suitable leaving groups include, but are not limited to, halogen, such as chloride and bromide and sulfonate esters, such as mesylate, tosylate, and triflate. According to Scheme 7, Compound C-1 is treated with 2,5-dimethoxytetrahydrofuran and acetic acid to yield Compound C-2. Then, an aromatic formylation is performed on Compound C-2 to yield Compound C-3. A representative reaction to perform an aromatic formylation uses DMF and $POCl_3$. Other aromatic formylation reactions include the Reimer-Tiemann reaction using chloroform and a strong base and the Duff reaction using hexaamine and an acid. Then, Compound C-3 undergoes a cyclization reaction where the aldehyde displaces the leaving group $LG^2$. The aldehyde of Compound C-3 is reduced and the oxygen nucleophilically displaces the leaving group. The reduction of the aldehyde can be performed with various reduction agents, such as sodium borohydride, lithium aluminum hydride, sodium triacetoxyborohydride, and zinc borohydride. Then, the nitro group of Compound C-4 is reduced to yield Compound C-5. Suitable reduction methods to convert the nitro group to an amino group include catalytic hydrogenation or reduction agents. Representative methods include catalytic hydrogenation using platinum oxide, Raney nickel or palladium hydroxide, iron metal in acidic media, such as refluxing acetic acid or samarium diiodide.

A representative synthesis for Compounds 3-B is shown in Scheme 8.

According to Scheme 8, the carbonyl of Compound D-1 is converted to a thiocarbonyl to yield Compound D-2. The variable groups $R^3$ and $R^4$ are as defined herein with reference to formula (I). In principle any general thionating reagent can be used to introduce the thiocarbonyl of D-2. Suitable thionating reagents include Lawesson's reagent, Davy's reagent, and Belleau's reagent, and phosphorus pentasulfide. Methods to perform thionation reaction can be found in the following references: 1) Shridhar, D. R.; Jogibhukta, M.; Krishnan, V. S. H. IDPL Res. Cent., Indian Drugs and Pharm. Ltd., Hyderabad, India. Organic Preparations and Procedures International (1984), 16(2), 91-6; 2) Shridhar, D. R.; Jogibhukta, M.; Krishnan, V. S. H. Chem. Div., IDPL Res. Cent., Hyderabad, India. Indian Journal of Chemistry, Section B: Organic Chemistry Including Medicinal Chemistry (1982), 21B(2), 130-3; and 3) Sastry, C. V. Reddy; Rao, K. Srinivasa; Krishnan, V. S. H.; Rastogi, K.; Jain, M. L.; Narayan, G. K. A. S. S.; Reddi, G. S.; Singh, P. P.; Rao, C. Seshagiri; Junnarkar, A. Y. Chem. Div., Indian Drugs and Pharm. Ltd., Hyderabad, India. Indian Journal of Chemistry, Section B: Organic Chemistry Including Medicinal Chemistry (1990), 29B(4), 396-8.

Compound D-2 is converted to Compound D-3 through tetrazole synthetic methods. Reaction of Compound D-2 with an azide with a suitable catalyst can form a tetrazole. Suitable azide compounds for reaction with D-2, include sodium azide and trimethylsilyl azide. Various catalysts can be use and suitable ones include mercuric acetate, zinc bromide, and zinc triflate. One method of forming tetrazoles such as D-3 can be found in the following reference: Nelson, Derek W.; Gregg, Robert J.; Kort, Michael E.; Perez-Medrano, Arturo; Voight, Eric A.; Wang, Ying; Grayson, George; Namovic, Marian T.; Donnelly-Roberts, Diana L.; Niforatos, Wende; Honore, Prisca; Jarvis, Michael F.; Faltynek, Connie R.; Carroll, William A. Neuroscience Research, Global Pharmaceutical Research and Development, Abbott Laboratories, Abbott Park, Ill., USA. Journal of Medicinal Chemistry (2006), 49(12), 3659-3666.

The nitro group of Compound D-3 is reduced to yield Compound D-4. Suitable reduction methods to convert the nitro group to an amino group include catalytic hydrogenation or reduction agents. Representative methods include catalytic hydrogenation using platinum oxide, Raney nickel or palladium hydroxide, iron metal in refluxing acetic acid, or samarium diiodide.

Pharmaceutical Compositions

The disclosed compounds are useful, at least, for the inhibition of PKC activity and the treatment of a disease or disorder that is mediated through the activity of a PKC activity. Accordingly, pharmaceutical compositions comprising at least one disclosed compound are also described herein.

A pharmaceutical composition comprising a subject compound may be administered to a patient alone, or in combination with other supplementary active agents. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

A subject compound may be administered to the host using any convenient means capable of resulting in the desired reduction in disease condition or symptom. Thus, a subject compound can be incorporated into a variety of formulations for therapeutic administration. More particularly, a subject compound can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Formulations for pharmaceutical compositions are well known in the art. For example, Remington's Pharmaceutical Sciences, by E. W. Martin, Mack Publishing Co., Easton, Pa., 19th Edition, 1995, describes exemplary formulations (and components thereof) suitable for pharmaceutical delivery of disclosed compounds. Pharmaceutical compositions comprising at least one of the subject compounds can be formulated for use in human or veterinary medicine. Particular formulations of a disclosed pharmaceutical composition may depend, for example, on the mode of administration and/or on the location of the infection to be treated. In some embodiments, formulations include a pharmaceutically acceptable carrier in addition to at least one active ingredient, such as a subject compound. In other embodiments, other medicinal or pharmaceutical agents, for example, with similar, related or complementary effects on the affliction being treated can also be included as active ingredients in a pharmaceutical composition.

Pharmaceutically acceptable carriers useful for the disclosed methods and compositions are conventional in the art. The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin or plasma preparations.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The disclosed pharmaceutical compositions may be formulated as a pharmaceutically acceptable salt of a disclosed compound. Pharmaceutically acceptable salts are non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydroiodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicylic acid, formic acid, trichloroacetic acid, trifluoroacetic acid, gluconic acid, asparagic acid, aspartic acid, benzenesulfonic acid, p-toluenesulfonic acid, naphthalenesulfonic acid, and the like. Lists of other suitable pharmaceutically acceptable salts are found in Remington's Pharmaceutical Sciences, 17th Edition, Mack Publishing Company, Easton, Pa., 1985. A pharmaceutically acceptable salt may also serve to adjust the osmotic pressure of the composition.

A subject compound can be used alone or in combination with appropriate additives to make tablets, powders, granules or capsules, for example, with conventional additives, such as lactose, mannitol, corn starch or potato starch; with binders, such as crystalline cellulose, cellulose derivatives, *acacia*, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The preparation may also be emulsified or the active ingredient encapsulated in liposome vehicles. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

In some embodiments, a subject compound can be delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

A subject compound can be utilized in aerosol formulation to be administered via inhalation. A subject compound can be formulated into pressurized acceptable propellants such as dichlorodifluoromethane, propane, nitrogen and the like.

Furthermore, a subject compound can be made into suppositories by mixing with a variety of bases such as emulsifying bases or water-soluble bases. A subject compound can be administered rectally via a suppository. The suppository can include vehicles such as cocoa butter, carbowaxes and polyethylene glycols, which melt at body temperature, yet are solidified at room temperature.

The term "unit dosage form," as used herein, refers to physically discrete units suitable as unitary dosages for human and animal subjects, each unit containing a predetermined quantity of a subject compound calculated in an amount sufficient to produce the desired effect in association with a pharmaceutically acceptable diluent, carrier or vehicle. The specifications for a subject compound depend on the particular compound employed and the effect to be achieved, and the pharmacodynamics associated with each compound in the host.

The dosage form of a disclosed pharmaceutical composition will be determined by the mode of administration chosen. For example, in addition to injectable fluids, topical or oral dosage forms may be employed. Topical preparations may include eye drops, ointments, sprays and the like. Oral formulations may be liquid (e.g., syrups, solutions or suspensions), or solid (e.g., powders, pills, tablets, or capsules). Methods of preparing such dosage forms are known, or will be apparent, to those skilled in the art.

Certain embodiments of the pharmaceutical compositions comprising a subject compound may be formulated in unit dosage form suitable for individual administration of precise dosages. The amount of active ingredient administered will depend on the subject being treated, the severity of the affliction, and the manner of administration, and is known to those skilled in the art. Within these bounds, the formulation to be administered will contain a quantity of the extracts or compounds disclosed herein in an amount effective to achieve the desired effect in the subject being treated.

Each therapeutic compound can independently be in any dosage form, such as those described herein, and can also be administered in various ways, as described herein. For example, the compounds may be formulated together, in a single dosage unit (that is, combined together in one form such as capsule, tablet, powder, or liquid, etc.) as a combination product. Alternatively, when not formulated together in a single dosage unit, an individual subject compound may be administered at the same time as another therapeutic compound or sequentially, in any order thereof.

The subject compound can be administered in combination with another protein kinase inhibitor. For example, the subject compound can be administered with a Syk kinase inhibitor. Various compounds that inhibit Syk kinase or Syk/Flt-3 kinase activity can be used in the methods described herein. These include, among others, small organic molecules, peptides or proteins, or nucleic acids. As used herein, a "Syk inhibitor" or "Syk kinase inhibitory compound" refers to any compound that directly inhibits the activity of Syk kinase itself or inhibits Syk interaction with other cellular targets needed for proper Syk function in the $IC_{50}$ range described herein. Inhibitors as used herein include the classical description of enzyme inhibitors, such as competitive, noncompetitive and uncompetitive inhibitors, and thus encompasses compounds that inhibit Syk kinase activity by, for example, binding to Syk kinase so as to inhibit access of a substrate to an active site, binding to Syk kinase so as to distort the active site to reduce binding to substrate, and/or bind a Syk kinase-substrate complex. Compounds that are Syk inhibitors are generally those that display an $IC_{50}$ with respect to a Syk kinase activity, such as the ability of Syk kinase to phosphorylate a synthetic or endogenous substrate, in an in vitro or cellular assay, in the range of about 5 µM or lower, about 1 µM or lower, about 500 nm or lower, about 100 nM or lower, about 50 nM or lower, about 10 mM or lower, or about 1 nM or lower. For instance, exemplary Syk inhibitor compounds are disclosed in U.S. application Ser. No. 10/631,029 and PCT publication WO 2004/014382. Both U.S. application Ser. No. 10/631,029 and PCT publication WO 2004/014382 are incorporated herein by reference. Skilled artisans will appreciate that compounds exhibiting lower $IC_{50}$, such as in the range of about 100 nM, 10 nM, 1 nM, or even lower, are useful for the methods herein.

Methods of Administration

The subject compounds can inhibit a protein kinase C activity. Accordingly, the subject compounds are useful for treating a disease or disorder that is mediated through the activity of a PKC activity in a subject. Accordingly, the subject compounds are useful for treating a disease or disorder that is associated with the activation of T-cells in a subject.

The route of administration will be selected according to a variety of factors including, but not necessarily limited to, the condition to be treated, the formulation and/or device used, the patient to be treated, and the like. Routes of administration useful in the disclosed methods include but are not limited to oral and parenteral routes, such as intravenous (iv), intraperitoneal (ip), rectal, topical, ophthalmic, nasal, and transdermal. Formulations for these dosage forms are described herein.

An effective amount of a subject compound will depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (host) being treated. For example, this may be the amount of a subject compound necessary to prevent, inhibit, reduce or relieve a disease or disorder that is mediated through the activity of a PKC activity in a subject. Ideally, a therapeutically effective amount of a compound is an amount sufficient to prevent, inhibit, reduce or relieve a disease or disorder that is mediated through the activity of a PKC activity in a subject without causing a substantial cytotoxic effect on host cells.

Therapeutically effective doses (or growth inhibitory amounts) of a subject compound or pharmaceutical composition can be determined by one of skill in the art, with a goal of achieving local (e.g., tissue) concentrations that are at least as high as the $IC_{50}$ of an applicable compound disclosed herein.

An example of a dosage range is from about 0.1 to about 200 mg/kg body weight orally in single or divided doses. In particular examples, a dosage range is from about 1.0 to about 100 mg/kg body weight orally in single or divided doses, including from about 1.0 to about 50 mg/kg body weight, from about 1.0 to about 25 mg/kg body weight, from about 1.0 to about 10 mg/kg body weight (assuming an average body weight of approximately 70 kg; values adjusted accordingly for persons weighing more or less than average). For oral administration, the compositions are, for example, provided in the form of a tablet containing from about 50 to about 1000 mg of the active ingredient, particularly about 75 mg, about 100 mg, about 200 mg, about 400 mg, about 500 mg, about 600 mg, about 750 mg, or about 1000 mg of the active ingredient for the symptomatic adjustment of the dosage to the subject being treated. In one exemplary oral dosage regimen, a tablet containing from about 500 mg to about 1000 mg active ingredient is administered once (e.g., a loading dose) followed by administration of ½ dosage tablets (e.g., from about 250 to about 500 mg) each 6 to 24 hours for at least 3 days.

The specific dose level and frequency of dosage for any particular subject may be varied and will depend upon a variety of factors, including the activity of the subject compound, the metabolic stability and length of action of that compound, the age, body weight, general health, sex and diet of the subject, mode and time of administration, rate of excretion, drug combination, and severity of the condition of the host undergoing therapy.

The present disclosure also contemplates combinations of one or more disclosed compounds with one or more other agents or therapies useful in the treatment of a disease or disorder. In certain instances, the disease or disorder is mediated through the activity of a PKC activity in a subject. In certain instances, the disease or disorder is cell proliferative disorder. For example, one or more disclosed compounds may be administered in combination with effective doses of other medicinal and pharmaceutical agents, or in combination other non-medicinal therapies, such as hormone or radiation therapy. The term "administration in combination with" refers to both concurrent and sequential administration of the active agents.

Protein Kinase C

PKC is a family of enzymes that function as serine/threonine kinases. The isoenzymes of PKC differ in their tissue distribution, enzymatic selectivity, requirement for $Ca^{2+}$, and regulation. PKCs play an important role in cell-cell signaling, gene expression and in the control of cell differentiation and growth.

The subject compound can be a selective inhibitor of PKC, e.g. an inhibitor selective for PKC over one or more other protein kinases, e.g. over one or more tyrosine kinases, for instance, over one or more non-receptor or receptor tyrosine kinases, e.g. over one or more of PKA, PKB, Abl, Met, Src, Ins-R, Flt-3, JAK-2, KDR and/or Ret proteins. The selective PKC inhibitors may optionally be selective over one or more serine/threonine kinases, e.g. one or more serine/threonine kinases which do not belong to the CDK family. The subject compounds can exhibit a selectivity of at least 10 fold, or 20 fold, or 100 fold for the PKC over one or more other protein kinases, e.g. over one or more tyrosine kinases, e.g. over Flt-3, JAK-2, KDR and/or Ret proteins, or over one or more serine/threonine kinases which do not belong to the CDK family.

The selectivity of a selective inhibitor of PKC over other protein kinases may be calculated as the ratio of the $IC_{50}$ measured for PKC in an assay described herein over the $IC_{50}$ determined for another kinase. In a certain instance, there is provided a PKC inhibitor for which the ratio of the $IC_{50}$ value as determined in an Allogeneic Mixed Lymphocyte Reaction (MLR) assay to the $IC_{50}$ value as determined in a BM assay is higher than 5, 10, 20, or 30. MLR and BM assays can be done according to known methods, e.g. mouse or human MLR and BM assays, such as disclosed herein.

The disclosure provides an inhibitor of PKC, which can be an isozyme-selective PKC inhibitor, wherein the subject compound possesses selectivity for the isoforms θ and α of PKC over one or more of the other PKC isoforms. In a certain instance, the subject compound possesses selectivity for the isoform θ of PKC over one or more of the other PKC isoforms. In a certain instance, the subject compound possesses selectivity for the isoform α of PKC over one or more of the other PKC isoforms. In one embodiment, the disclosed compounds exhibit selectivity for PKC θ and PKC α over at least one PKC isoform.

A subject compound can show a selectivity of at least 10 fold, or 20 fold, or 100 fold for the isoforms θ or α of PKC over one or more of the other PKC isoforms. Selectivity for the isoforms θ or α of PKC over one or more of the other PKC isoforms can be measured by comparing the $IC_{50}$ of the subject compound for the isoforms θ or α of PKC to the $IC_{50}$ of the subject compound for the other PKC isoforms. In a certain instance, the selectivity can be determined by calculating the ratio of $IC_{50}$ of the subject compound for the other isoforms of PKC to the $IC_{50}$ of the subject compound for θ or α isoforms of PKC. In certain examples subject compounds exhibit a selectivity for PKC θ, α or both over another PKC isoform of at least about 2-fold, such as from about 3-fold to about 300-fold, from about 10-fold to about 100-fold or from about 5-fold to 50-fold. $IC_{50}$ values are obtained, for example, according to PKC assays described herein. The subject compounds can show an $IC_{50}$ value for the isoforms θ or α of PKC of 1 µM or less, such as less than about 300 nM, such as from about 1 nM to about 250 nM, less than 100 nM or even less than 10 nM in the assays disclosed herein.

The subject compounds can show a selectivity of the isoforms θ or µ of PKC over other isoforms of PKC, as well as a selectivity over one or more of the other protein kinases, e.g. over one or more tyrosine kinases, or over one or more serine/threonine kinases which do not belong to the CDK-family, e.g. over one or more of PKA, PKB, Abl, Met, Src, Ins-it, Flt-3, JAK-2, KDR and Ret proteins, e.g. over one or more of Flt-3, JAK-2, KDR and Ret proteins.

Certain isozymes of PKC have been implicated in the mechanisms of various disease states, including, but not necessarily limited to, the following: cancer (PKC α, βI, βII, and δ); cardiac hypertrophy and heart failure (PKC βI and PKC βII) nociception (PKC γ and ε); ischemia including myocardial infarction (PKC ε and δ); immune response, particularly T-cell mediated (PKC θ and α); and fibroblast growth and memory (PKC δ and ζ). The role of PKC ε is also implicated in pain perception. PKC inhibitors can also be used for treating an ocular disease or disorder involving inflammatory and/or neovascular events.

The subject compounds can be used in the treatment of mammalian (especially human) disease states characterized by aberrant, elevated activity of a PKC isozyme in a tissue as compared to non-disease tissue of the same origin. PKC isozymes and disease states and/or biological functions amenable to therapy by inhibition of activity of the PKC isozyme include, but are not necessarily limited to: PKC α (hyperproliferative cellular diseases, such as cancer); PKC βI and PKC βII (cardiac hypertrophy and heart failure); PKC γ (pain management); PKC δ (ischemia, hypoxia (e.g., such as in myocardial infarction and in stroke); apoptosis induced by UV irradiation; and aberrant fibroblast growth (e.g., as may occur in wound healing)); PKC ε (pain management, myocardial dysfunction); PKC θ (immune system diseases, particularly those involving T-cell mediated responses); and PKC ζ (memory and fibroblast growth).

PKC Theta

PKC θ is expressed predominantly in lymphoid tissue and skeletal muscle. PKC θ is selectively expressed in T-cells and plays a role in mature T-cell activation. It has been shown that PKC θ is involved in T-cell receptor (TCR)-mediated T-cell activation but inessential during TCR-dependent thymocyte development. PKC θ, but not other PKC isoforms, translocates to the site of cell contact between antigen-specific T-cells and antigen presenting cells (APC), where it localizes with the TCR in the central core of the T-cell activation. PKC θ, but not the α, ε, or ζ isoenzymes, can selectively activate a FasL promoter-reporter gene and upregulate the mRNA or cell surface expression of endogenous FasL. On the other hand, PKC θ and ε can promote T-cell survival by protecting the cells from Fas-induced apoptosis, and this protective effect was mediated by promoting p90Rsk-dependent phosphorylation of BCL-2 family member BAD. Thus, PKC θ appears to play a dual regulatory role in T-cell apoptosis.

PKC θ inhibitors can find use in the treatment or prevention of disorders or diseases mediated by T lymphocytes, for example, autoimmune disease such as rheumatoid arthritis, psoriasis and lupus erythematosus, and inflammatory disease such as asthma and inflammatory bowel diseases.

PKC θ is a drug target for immunosuppression in transplantation and autoimmune diseases (Isakov et al. (2002) Annual Review of Immunology, 20, 761-794). PCT Publication WO2004/043386 identifies PKC θ as a target for treatment of transplant rejection and multiple sclerosis. PKC θ also plays a role in inflammatory bowel disease (The Journal of Pharmacology and Experimental Therapeutics (2005), 313 (3), 962-982), asthma (WO 2005062918), and lupus (Current Drug Targets: Inflammation & Allergy (2005), 4 (3), 295-298).

In addition, PKC θ is highly expressed in gastrointestinal stromal tumors (Blay, P. et al. (2004) Clinical Cancer Research, 10, 12, Pt. 1), it has been suggested that PKC θ is a molecular target for treatment of gastrointestinal cancer (Wiedmann, M. et al. (2005) Current Cancer Drug Targets 5(3), 171).

Experiments induced in PKC θ knock-out mice led to the conclusion that PKC 0 inactivation prevented fat-induced defects in insulin signalling and glucose transport in skeletal muscle (Kim J. et al, 2004, The J. of Clinical Investigation 114 (6), 823). This data indicates PKC θ is a therapeutic target for the treatment of type 2 diabetes, and hence PKC θ inhibitors can be useful for treating such disease.

Syk Kinase

As disclosed herein, the subject compound can be administered in combination with another protein kinase inhibitor, such as a Syk kinase inhibitor.

"Syk" or "Syk kinase" refers to the 72 kDa non-receptor (cytoplasmic) spleen protein tyrosine kinase expressed in B-cells and other hematopoetic cells. Syk kinase is characterized by two consensus Src-homology 2 (SH2) domains in tandem that bind to phosphorylated immunoreceptor tyrosine-based activation motifs ("ITAMs"), a "linker" domain and a catalytic domain (for a review, see Sada et al., 2001, J. Biochem. (Tokyo) 130:177-186 and also Turner et al., 2000, Immunology Today 21:148-154 and Wong et al., 2004, Expert Opin Investig Drugs 13(7):743-62.). Syk kinase is also critical for tyrosine phosphorylation of multiple proteins which regulate important pathways leading from immunoreceptors, such as $Ca^{2+}$ mobilization and mitogen-activated protein kinase (MAPK) cascades and degranulation. Syk kinase also plays a critical role in integrin signaling in neutrophils (see, e.g., Mocsai et al. 2002, Immunity 16:547-558). Syk kinase includes kinases from any species of animal, including but not limited to, *homo sapiens*, simian, bovine, porcine, rodent, etc., recognized as belonging to the Syk family. Specifically included are isoforms, splice variants, allelic variants, mutants, both naturally occurring and man-made. The amino acid sequences of such Syk kinases are available from GENBANK. Specific examples of mRNAs encoding different isoforms of human Syk kinase are available at GENBANK accession no. gi|21361552|ref|$_{NM}$-003177.2, gi|496899|emb|Z29630.1|HSSYKPTK[496899] and gi|15030258|gb|BC011399.1|BC011399[15030258], which are incorporated herein by reference.

Therapeutic Applications

The subject compounds are useful for treating a disease or disorder that is mediated through, or exacerbated by, the activity of a PKC in a subject in need of treatment. Also, the compounds are useful for treating a disease or disorder that is associated with aberrant or otherwise undesirable T cell activation in a subject.

Accordingly, the present disclosure provides methods of treating an inflammatory disease in a subject by administering an effective amount of a subject compound, including a salt or solvate or stereoisomer thereof, so as to treat inflammation. Inflammatory diseases contemplated for therapy include acute and chronic inflammation mediated or exacerbated by PKC activity The present disclosure also provides methods of treating an autoimmune disease in a subject by administering to the subject an effective amount of a subject compound, including a salt or solvate or stereoisomer thereof, so as to treat the autoimmune disease.

The present disclosure also provides methods of treating an ocular disease or disorder involving inflammatory and/or neovascular events by administration of a subject compound, including a salt or solvate or stereoisomer thereof, in an effective amount.

Diseases or conditions of interest for treatment according to the present disclosure include, but are not limited to, atherosclerosis, vascular occlusion due to vascular injury such as angioplasty, restenosis, obesity, syndrome X, impaired glucose tolerance, polycystic ovary syndrome, hypertension, heart failure, chronic obstructive pulmonary disease, CNS diseases such as Alzheimer disease or amyotrophic lateral sclerosis, cancer, infectious diseases such as: AIDS, septic shock or adult respiratory distress syndrome, ischemia/reperfusion injury, e.g.: myocardial infarction, stroke, gut ischemia, renal failure or hemorrhage shock, and traumatic shock, e.g. traumatic brain injury.

Further diseases or conditions of interest for treatment according to the present disclosure include, but are not limited to, T-cell mediated acute or chronic inflammatory diseases or disorders or autoimmune diseases, rheumatoid arthritis, osteoarthritis, systemic lupus erythematosus, Hashimoto's thyroidis, multiple sclerosis, myasthenia gravis, diabetes type I or II and the disorders associated therewith, transplant rejection, graft versus host disease, respiratory diseases, asthma, inflammatory lung injury, inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases (such as Sjoegren's syndrome, keratoconjunctivitis, uveitis) inflammatory bowel disease, Crohn's disease or ulcerative colitis, Guillain-Barre syndrome, and allergies.

The subject compounds can also be used for preventing or treating or delaying ocular diseases and disorders involving inflammation and/or neovascularization. Ocular diseases or disorders involving inflammatory and/or neovascular events include, but are not limited to, macular degeneration (AMD), diabetic ocular diseases or disorders, uveitis, optic neuritis, ocular edema, ocular angiogenesis, ischemic retinopathy, anterior ischemic optic neuropathy, optic neuropathy and neuritis, macular edema, cystoid macular edema (CME), retinal disease or disorder, such as retinal detachment, retinitis pigmentosa (RP), Stargart's disease, Best's vitelliform retinal degeneration, Leber's congenital amaurosis and other hereditary retinal degenerations, Sorsby's fundus dystrophy, pathologic myopia, retinopathy of prematurity (ROP), Leber's hereditary optic neuropathy, corneal transplantation or refractive corneal surgery, keratoconjunctivitis, or dry eye.

Generally, cell proliferative disorders treatable with the subject compound disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, breast cancer, ovarian cancer, renal cancer, gastrointestinal cancer, kidney cancer, bladder cancer, pancreatic cancer, lung squamous carcinoma, and adenocarcinoma.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blaire et al., 1997, Blood 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34;22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, Blood 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., Proc. Natl. Acad. Sci. USA, 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma.

In some embodiments, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9;22)(qq34;q11)), chronic neutrophilic leukemia, chronic eosinophilic leukemia/hypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome with t(9;12)(q22;p12) (TEL-Syk fusion; see, e.g., Kuno et al., 2001, Blood 97:1050).

In some embodiments, the composition can be used to treat acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21) (q22;q22), AML1(CBF-alpha)/ETO, Acute promyelocytic leukemia (AML with t(15;17)(q22;q11-12) and variants, PML/RAR-alpha), AML with abnormal bone marrow eosinophils (inv(16)(p13q22) or t(16;16)(p13;q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

In other aspects, cell proliferative disorders comprise virally mediated tumors. These can arise from infection of cells by an oncogenic virus that has the capability of transforming a normal cell into a tumor cell. Because rates of viral infection far exceed the number of actual incidence of cell transformation, viral mediated transformation generally act together with other cellular factors to generate a transformed tumor cell. Thus, a virally mediated tumor does not require the virus to be the sole causative agent of the cell proliferative disorder, but rather that the viral infection or persistent presence of virus is associated with the generation of the tumor. Generally, tumors where the causative agent is a virus typically has continual expression of a limited number of viral genes and that viral these oncogenes, expressed as part of the viral infection or through persistence of the virus, disrupts the normal cellular gene expression and signal transduction pathways. Without being bound by theory, viral oncogenes involved in cell transformation appear to disrupt four main cellular processes: cell surface receptors that interact with growth factors and extracellular matrix, transmembrane signaling networks, cytosolic elements such as soluble proteins and second messengers, and nuclear proteins including DNA binding proteins and factors which function directly and indirectly in gene regulation and replication.

In some embodiments, the virally mediated tumor treatable with the subject compound disclosed herein is associated with any virus that encodes an immunoreceptor tyrosine-based activation motif (ITAM) capable of modulating Syk activity. This motif, as noted above, refers to a conserved amino acid sequence motif that functions by interacting with and activating nonreceptor tyrosine kinases. ITAM motifs are found in, among others, the p and y chains of FcεRI, the ε subunit of the T cell receptor, and immunoglobulin β (Igfβ) and Igα of the B cell receptor. The canonical sequence motif is typically Yxx(L/I)x.sub.6-8Yxx(L/I), where x represents any amino acid. Generally, the tyrosine residues in the motif are involved in ITAM signaling and are substrates for phosphorylation by Src family of kinases. The phosphorylated form of ITAMs function as interaction sites for SH2 (src homology domain) containing signaling proteins, such as Syk/ZAP-70 kinases. In addition to its presence in a variety of cellular cell surface molecules, the ITAM sequences have been identified in virally encoded proteins. In view of the descriptions herein indicating function of Syk kinase as an oncogene, tumors associated with viruses carrying genes encoding proteins with ITAM sequences can be treated with Syk inhibitor compounds.

Accordingly, in some embodiments, the virally mediated tumor treatable with the subject compounds is associated with Kaposi's sarcoma (KS) associated herpes virus, a lymphotropic virus implicated in Kaposi's sarcoma, a rare malignancy found at higher incidence among HIV infected population. The KS associated herpes virus encodes a transmembrane protein termed KI having an immunoreceptor tyrosine-based activation motif (ITAM)-like sequence. The KI gene product is thought to act in a constitutive manner through its cysteine-rich ectodomain to activate Syk and its related kinase Zap-70 (Lagunoff, M. et al., 1999, Proc. Natl. Acad. Sci. USA 96(10):5704-5709). In further support of the methods herein, transgenic mice bearing the KI gene appears to increase the incidence of certain sarcomas and lymphomas in an infected animal, indicating a role for KI activity in oncogenesis (Prakash et al., 2002, J. Natl. Cancer Inst. 94:926-35).

In some embodiments, the virally mediated tumor is associated with Epstein Barr Virus (EBV). Epstein Barr Virus is a member of the Herpesviridae family that, following primary infection, replicates in the epithelial cells of the oropharynx and infect recirculating B lymphocytes. Infection can lead to acute infectious mononucleosis, also known as glandular fever. Infectious mononucleosis is a benign lymphoproliferative disease characterized by transient immunosuppression and an expansion of atypical lymphocytes, the majority of which are $CD8^{+T}$ cells. In these T cells, EBV establishes a latent but persistent infection during which a select set of viral genes are expressed. The entire genome can persist in the proliferating lymphocytes as episomal DNA. EBV infection is associated with Burkitt's lymphoma, Hodgkin's lymphoma, and adult T cell leukemia.

The LMP2A protein encoded by the EBV genome is a transmembrane protein thought to play a role in maintaining the latency of the EBV virus following infection. It consists of an extended amino terminal tail, 12 membrane spanning domains, and a cytoplasmic domain. The amino terminal region contains the ITAM motif, which allows interaction of LMP2A with Syk kinase (Fruehling et al., 1997, Virology, 235:241-251). LMP2A appears to regulate Syk kinase in lymphoid cells to promote B-cell survival and maintain latency. Because Syk plays a role in the signal transduction pathways that regulate other signaling pathways, such as PI-3K, BLNK, and phospholipase y2 and is involved in enhancing lymphoid cell survival, improper Syk activation through LMP2A protein or other virally mediated effectors may play a role in inducing aberrant lymphoproliferation (Caldwell et al., 2000, J Virol 74(19):9115; Caldwell et al., 1998, Immunity 9:405)).

In some embodiments, the virally mediated tumor to be treated with the subject composition is associated with Human T-cell Lymphotropic Virus (HTLV-1 virus), a retrovirus in the same class of virus as the AIDS virus, HIV-1. The virus is tropic for $CD4^{+T}$-cells although $CD8^{+T}$-cells can also serve as a viral reservoir. HTLV-1 infection is associated with, among others, adult T-cell Leukemia/lymphoma (ATLL) and a number of other lymphocyte disorders. During HTLV-1 infection, Syk is expressed in infected cells while expression of the Syk related kinase, ZAP-70, is absent (Weil et al., 1999, J. Virol. 73(5):3709-17). Dysregulation of a number of kinases, including Syk, is implicated in HTLV-1 mediated induction of adult T-cell leukemia.

In some embodiments, the virally mediated tumor is associated with mammary tumor virus (MTV). ITAM sequences are found within the Env gene of murine mammary tumor virus (MMTV), a B type retrovirus identified as an etiological agent for breast cancer in mice. Mouse mammary epithelial cells transfected with MMTV Env gene display characteristics of a transformed phenotype, such as colony formation in soft agar and invasiveness in basement membrane preparations (Katz et al., 2005, J Exp Med. 201(3):431-9). Murine mammary tumor virus-like sequences are also present in human cancers, such as breast cancer and T cell lymphomas (Wang et al., 2000, Clinical Cancer Res. 6:1273-1278), and correlated with tumorigenesis as these sequences are not observed in the majority of normal breast tissue.

It is to be understood that use of subject composition for treating virally mediated tumors is not limited to tumors associated with the viruses specified above. As noted, any tumors associated with an oncogenic virus in which Syk is activated as part of its oncogenic mechanism, whether or not it involves ITAM sequences, can be targeted using the subject compounds.

Characterization of Functional Properties

The following are exemplary assays useful in characterizing activities of a compound of interest.

A. In Vitro

1. Protein Kinase C Assay

The inhibition of PKC activity was measured by monitoring the production of phosphorylated peptide by fluorescence polarization at different concentrations of the inhibitor. Reactions were carried out in 96-well plate format with a total volume of 20 µL containing 20 mM HEPES, pH 7.4, 5 mM $MgCl_2$, 0.2 mM $CaCl_2$, 1 mM DTT, 0.02% Brij-35, 0.1 mg/mL phosphatidylserine, 0.02 mg/mL dioleoyl-sn-glycerol and 5 µM each of ATP and the peptide substrate. Compounds were first diluted serially in DMSO and then transferred to a solution containing the above concentrations of HEPES, $MgCl_2$, $CaCl_2$, DTT, and Brij-35 to yield 5× compound solutions in 2% DMSO, which was then added to the reaction solution. Reactions were initiated by the addition of PKC at a typical concentration as described in the table below, and then allowed to incubate at room temperature for 20 minutes. At the end of this time, a combination of quench (EDTA) and detection (peptide tracer and antibody) reagents was added using the protocol of Invitrogen P2748 (Carlsbad, Calif.), a Protein Kinase C Fluorescence polarization Assay Kit. After a 30 minute period of incubation, the amount of phosphorylated peptide generated was measured by fluorescence polarization (Ex=485 nm, Em=535 nm) using a Tecan Polarian instrument (Switzerland).

TABLE 4

| | Peptide substrate | SEQ ID | Enzyme source | enzyme concentration |
|---|---|---|---|---|
| PKC theta | RFARKGSLRQKNV | Seq ID No. 1 | Upstate Biotechnologies, Temecula, CA, cat. #14-444 | 40 ng/mL |
| PKC epsilon | RFARKGSLRQKNV | Seq ID No. 1 | Upstate Biotechnologies, Temecula, CA, cat. #14-518 | 50 ng/mL |

2. IL-2 ELISA, Human Primary T Cell, Anti-CD3+CD28+ Assays

Human Primary T Cell Isolation and Culture:

Human primary T cells were prepared as follows. Whole blood was obtained from a healthy volunteer, mixed 1:1 with PBS, layered on to Ficoll Hypaque (Amersham Pharmacia Biotech, Piscataway, N.J., Catalog #17-1440-03) in 2:1 blood/PBS:ficoll ratio and centrifuged for 30 minutes at 4° C. at 1750 rpm. The cells at the serum:ficoll interface were recovered and washed twice with 5 volumes of PBS. These freshly isolated human peripheral blood mononuclear cells were cultured in Yssel's medium containing 40 U/mL IL2 in a flask pre-coated with 1 µg/mL αCD3 and 5 µg/mL αCD28 (Anti-Human CD3, BD Pharmingen Catalog #555336, Anti-Human CD28, Beckman Coulter Catalog #1M1376). The cells were stimulated for 3-4 days, then transferred to a fresh flask and maintained in RPMI (RPMI-1640 with L-Glutamine; Mediatech, Inc., Herndon Va., cat. #10-040-CM) with 10% FBS and 40 U/mL IL-2. The primary T-cells were then washed twice with PBS to remove the IL-2.

Primary T Cell Stimulation and IL2 ELISA:

Human primary T cells (100,000 cells per well) were pre-incubated with or without test compound in Yssel's medium for 1 hr at 37° C. Cells were then stimulated by transferring them to round-bottom 96-well plates pre-coated with 1 µg/ml αCD3 and 5 µg/ml αCD28. For counter assay, cells were instead stimulated by adding 8× stock solutions of PMA and ionomycin in Yssels (for final concentrations of 0.5 ng/ml PMA and 0.1 µM ionomycin, both from Calbiochem). Cells were incubated at 37° C. for 24 hours before 100 µL supernatants were harvested for quantification of IL-2 by ELISA using Human IL-2 Duoset ELISA Kit from R and D Systems, Cat. # DY202E.

3. Protein Kinase C Assay

The subject compounds can be tested for activity on different PKC isoforms according to the following method.

Assay is performed in a white with clear bottom 384-well microtiterplate with non-binding surface. The reaction mixture (25 µl) contains 1.5 µM of a tridecapeptide acceptor substrate that mimics the pseudo substrate sequence of PKC α with the Ala→Ser replacement, 10 µM $^{33}$P-ATP, 10 mM Mg(NO$_3$)$_2$, 0.2 mM CaCl$_2$, PKG at a protein concentration varying from 25 to 400 ng/ml (depending on the isotype used), lipid vesicles (containing 30 mol % phosphatidylserine, 5 mol % DAG and 65 mol % phosphatidylcholine) at a final lipid concentration of 0.5 mM, in 20 mM Tris-HCl buffer pH 7.4+0.1% BSA. Incubation is performed for 60 minutes at room temperature. Reaction is stopped by adding 50 µl of stop mix (100 mM EDTA, 200 µM ATP, 0.1% Triton X-100, 0.375 mg/well streptavidin-coated SPA beads in phosphate buffered saline w/o Ca, Mg. After 10 minutes incubation at room temperature, the suspension is spun down for 10 minutes at 300 g. Incorporated radioactivity is measured in a Trilux counter for 1 minute. IC$_{50}$ measurement is performed on a routine basis by incubating a serial dilution of inhibitor at concentrations ranging between 1-1000 µM. IC$_{50}$ values are calculated from the graph by curve fitting with XL Fit® software.

4. Protein Kinase C α Assay

Human recombinant PKC α is obtained from Oxford Biomedical Research and is used under the assay conditions as described under Section A.1 above.

5. Protein Kinase C β1 Assay

Human recombinant PKC β1 is obtained from Oxford Biomedical Research and is used under the assay conditions as described under Section A.1 above.

6. Protein Kinase C δ Assay

Human recombinant PKC δ is obtained from Oxford Biomedical Research and is used under the assay conditions as described under Section A.1 above.

7. Protein Kinase C ε Assay

Human recombinant PKC ε is obtained from Oxford Biomedical Research and is used under the assay conditions as described under Section A.1 above.

8. Protein Kinase C η Assay

Human recombinant PKC η is obtained from PanVera and is used under the assay conditions as described under Section A.1 above.

9. Protein Kinase C θ Assay

Human recombinant PKC θ is used under the assay conditions as described above.

10. CD28 Costimulation Assay

The assay is performed with Jurkat cells transfected with a human interleukin-2 promoter/reporter gene construct as described by Baumann G et al. in Transplant. Proc. 1992; 24:43-8, the β-galactosidase reporter gene being replaced by the luciferase gene (de Wet J., et al., Mol. Cell. Biol. 1987, 7(2), 725-737). Cells are stimulated by solid phase-coupled antibodies or phorbol myristate acetate (PMA) and the Ca$^{++}$ ionophore ionomycin as follows. For antibody-mediated stimulation Microlite TM1 microtiter plates (Dynatech) are coated with 3 µg/ml goat anti-mouse IgG Fc antibodies (Jackson) in 55 µl phosphate-buffered saline (PBS) per well for three hours at room temperature. Plates are blocked after removing the antibodies by incubation with 2% bovine serum albumin (BSA) in PBS (300 µl per well) for 2 hours at room temperature. After washing three times with 300 µl PBS per well, 10 ng/ml anti-T cell receptor antibodies (WT31, Becton & Dickinson) and 300 ng/ml anti-CD28 antibodies (15E8) in 50 µl 2% BSA/PBS are added as stimulating antibodies and incubated overnight at 4° C. Finally the plates are washed three times with 300 µl PBS per well. Seven three-fold serial dilutions of test compounds in duplicates in assay medium (RPMI 1640/10% fetal calf serum (FCS) containing 50 µM 2-mercaptoethanol, 100 units/ml penicillin and 100 µg/ml streptomycin) are prepared in separate plates, mixed with transfected Jurkat cells (clone K22 290_H23) and incubated for 30 minutes at 37° C. in 5% CO$_2$ 100 µl of this mixture containing 1×10$^5$ cells are then transferred to the antibody-coated assay plates. In parallel 100 µl are incubated with 40 ng/ml PMA and 2 µM ionomycin. After incubation for 5.5 hours at 37° C. in 5% CO$_2$, the level of luciferase is determined by bioluminescence measurement. The plates are centrifuged for 10 minutes at 500 g and the supernatant is removed by flicking. Lysis buffer containing 25 mM Tris-phosphate, pH 7.8, 2 mM DTT, 2 mM 1.2-diaminocyclohexane-N,N,N',N-tetraacetic acid, 10% (v/v) glycerol and 1% (v/v) Triton X-100 is added (20 µl per well). The plates are incubated at room temperature for 10 minutes under constant shaking. Luciferase activity is assessed with a bioluminescence reader (Labsystem, Helsinki, Finland) after automatic addition of 50 µl per well luciferase reaction buffer containing 20 mM Tricine, 1.07 mM (MgCO$_3$)$_4$Mg(OH)$_2$×5H$_2$O, 2.67 mM MgSO$_4$, 0.1 mM EDTA, 33.3 mM DTT, 270 µM coenzyme A, 470 µM luciferin (Chemie Brunschwig AG), 530 µM ATP, pH 7.8. Lag time is 0.5 seconds, total measuring time is 1 or 2 seconds. Low control values are light units from anti-T cell receptor- or PMA-stimulated cells, high controls are from anti-T cell receptor/anti-CD28- or PMA/ionomycin-stimulated cells without any test sample. Low controls are subtracted from all values. The inhibition obtained in the presence of a test compound is calculated as percent inhibition of the high control. The concentration of test compounds resulting in 50% inhibition (IC$_{50}$) is determined from the dose-response curves.

11. Bone Marrow Proliferation (BM) Assay

Bone marrow cells from CBA mice (2.5×104 cells per well in flat bottom tissue culture microtiter plates) are incubated in 100 µl RPMI medium containing 10% FCS, 100 U/ml penicillin, 100 µg/ml streptomycin (Gibco BRL, Basel, Switzerland), 50 tJM 2-mercaptoethanol (Fluke, Buchs, Switzerland), WEHI-3 conditioned medium (7.5% v/v) and L929 conditioned medium (3% v/v) as a source of growth factors and serially diluted compounds. Seven threefold dilution steps in duplicates per test compound are performed. After four days of incubation 1 µCi $^3$H-thymidine is added. Cells are harvested after an additional five-hour incubation period, and incorporated $^3$H-thymidine is determined according to standard procedures. Conditioned media are prepared as follows. WEHI-3 cells 1 (ATCC TIB68) and L929 cells (ATCC CCL 1) are grown in RPMI medium until confluence for 4 days and one week, respectively. Cells are harvested, resuspended in the same culture flasks in medium C containing 1% FCS (Schreier and Tees 1981) for WEHI-3 cells and RPMI medium for L929 cells and incubated for 2 days (WEHI-3) or one week (L929). The supernatant is collected, filtered through 0.2 µm and stored in aliquots at −80° C. Cultures without test compounds and without WEHI-3 and L929 supernatants are used as low control values. Low control values are subtracted from all values. High controls without any sample are taken as 100% proliferation. Percent inhibition by the samples is calculated and the concentrations required for 50% inhibition (IC$_{50}$ values) are determined.

12. Allogeneic Mixed Lymphocyte Reaction (MLR)

The two-way MLR is performed according to standard procedures (J. Immunol. Methods, 1973, 2, 279 and Meo T. et al., Immunological Methods, New York, Academic Press, 1979, 227-39). Briefly, spleen cells from CBA and BALB/c mice ($1.6 \times 10^5$ cells from each strain per well in flat bottom tissue culture microtiter plates, $3.2 \times 10^5$ in total) are incubated in RPMI medium containing 10% FCS, 100 U/ml penicillin, 100 µg/ml streptomycin (Gibco BRL, Basel, Switzerland), 50 µM 2-mercaptoethanol (Fluka, Buchs, Switzerland) and serially diluted compounds. Seven threefold dilution steps in duplicates per test compound are performed. After four days of incubation 1 µCi $^3$H-thymidine is added. Cells are harvested after an additional five-hour incubation period, and incorporated $^3$H-thymidine is determined according to standard procedures. Background values (low control) of the MLR are the proliferation of BALB/c cells alone. Low controls are subtracted from all values. High controls without any sample are taken as 100% proliferation. Percent inhibition by the samples is calculated, and the concentrations required for 50% inhibition ($IC_{50}$ values) are determined.

B. In Vivo

Heart Transplantation Model

The strain combination used: Male Lewis ($RT^1$ haplotype) and BN ($RT^1$ haplotype). The animals are anaesthetised using inhalational isofluorane. Following heparinisation of the donor rat through the abdominal inferior vena cava with simultaneous exsanguination via the aorta, the chest is opened and the heart rapidly cooled. The aorta is ligated and divided distal to the first branch and the brachiocephalic trunk is divided at the first bifurcation. The left pulmonary artery is ligated and divided and the right side divided but left open. All other vessels are dissected free, ligated and divided and the donor heart is removed into iced saline.

The recipient is prepared by dissection and cross-clamping of the infra-renal abdominal aorta and vena cava. The graft is implanted with end-to-side anastomoses, using 1010 monofilament suture, between the donor brachiocephalic trunk and the recipient aorta and the donor right pulmonary artery to the recipient vena cava. The clamps are removed, the graft tethered retroabdominally, the abdominal contents washed with warm saline and the animal is closed and allowed to recover under a heating lamp. Graft survival is monitored by daily palpation of the beating donor heart through the abdominal wall. Rejection is considered to be complete when-heart beat stops. Graft survival is monitored in animals treated with compounds.

Graft v. Host Model

Spleen cells ($2 \times 10^7$) from Wistar/F rats are injected subcutaneously into the right hind footpad of (Wistar/F× Fischer 344)$F_1$ hybrid rats. The left footpad is left untreated. The animals are treated with the test compounds on 4 consecutive days (0-3). The popliteal lymph nodes are removed on day 7, and the weight differences between two corresponding lymph nodes are determined. The results are expressed as the inhibition of lymph node enlargement (given in percent) comparing the lymph node weight differences in the experimental groups to the weight difference between the corresponding lymph nodes from a group of animals left untreated with a test compound. In certain instances the test compound is a selective PKC inhibitor. For example, disclosed compounds that are particularly useful for treating graft versus host disease and related disorders are selective PKC α and θ inhibitors.

Research Applications

Since subject compounds can inhibit a PKC activity, such compounds are also useful as research tools. The present disclosure also provides a method for using a compound of formula (I) or a salt or solvate or stereoisomer thereof as a research tool for studying a biological system or sample, or for discovering new chemical compounds that can inhibit a PKC activity.

The disclosure provides for a method of studying a biological system or sample known to comprise PKC, the method comprising: (a) contacting the biological sample with a compound of formula (I) or a salt or solvate or stereoisomer thereof; and (b) determining the inhibiting effects caused by the compound on the biological sample.

Any suitable biological sample having PKC can be employed in such studies which can be conducted either in vitro or in vivo. Representative biological samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest.

When used as a research tool, a biological sample comprising PKC is typically contacted with a PKC activity-inhibiting amount of a subject compound. After the biological sample is exposed to the compound, the effects of inhibition of a PKC activity are determined using conventional procedures and equipment, such as the assays disclosed herein. Exposure encompasses contacting the biological sample with the compound or administering the compound to a subject. The determining step can involve measuring a response (a quantitative analysis) or can involve making an observation (a qualitative analysis). Measuring a response involves, for example, determining the effects of the compound on the biological sample using conventional procedures and equipment, such as radioligand binding assays and measuring ligand-mediated changes in functional assays. The assay results can be used to determine the activity level as well as the amount of compound necessary to achieve the desired result, that is, a PKC activity-inhibiting amount.

Additionally, subject compounds can be used as research tools for evaluating other chemical compounds, and thus are also useful in screening assays to discover, for example, new compounds having a PKC inhibiting activity. In this manner, a subject compound can be used as a standard in an assay to allow comparison of the results obtained with a test compound and with the subject compounds to identify those test compounds that have about equal or superior activity, if any. For example, $IC_{50}$ data for a test compound or a group of test compounds is compared to the $IC_{50}$ data for a subject compound to identify those test compounds that have the desired properties, for example, test compounds having an $IC_{50}$ about equal or superior to a subject compound, if any.

This aspect includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with a subject compound to provide a second assay value; wherein step (a) is conducted either before, after or concurrently with step (b); and (c) comparing the first assay value from step (a) with the second assay value from step (b). The assays that can be used for generation of comparison data are disclosed herein, such as the PKC assays.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used.

Examples 1 and 2 was transferred to a separatory funnel and partitioned (EtOAc//H₂O). The organic phase was washed with H₂O (3×50 mL), brine (3×50 mL), dried over Na₂SO₄ and evaporated in vacuo to give a brown residue. The residue was purified by flash chromatography (hexanes 1:1 EtOAc/hexanes) to furnish the title compound as a white solid (1.2 g, 54%).

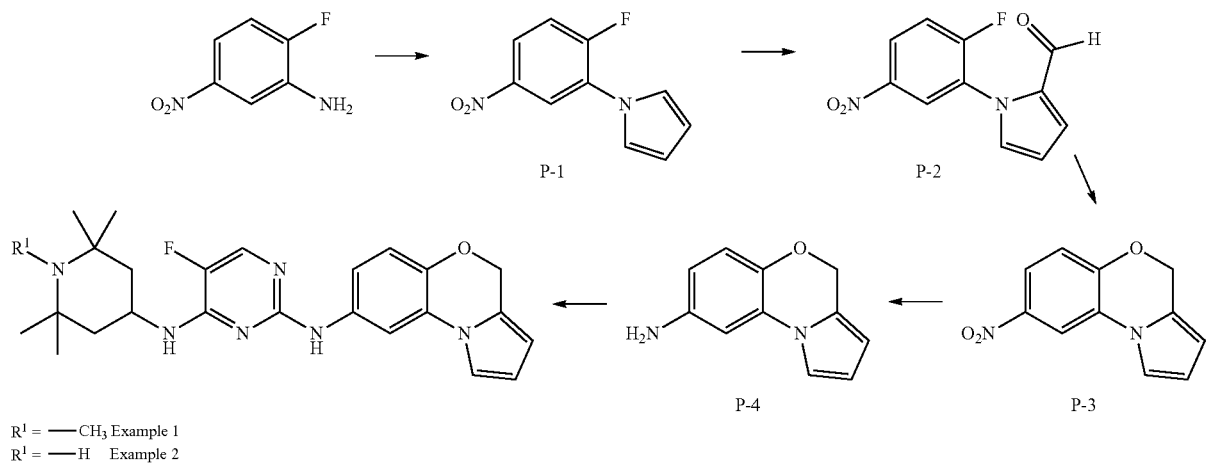

R¹ = —CH₃ Example 1
R¹ = —H  Example 2

Preparation 1

Synthesis of 1-(2-fluoro-5-nitrophenyl)-1H-pyrrole (P-1)

5-Nitro-2-fluoroaniline (7.0 g, 44.8 mmol) was taken up in acetic acid (60 mL) in a 250 mL round bottomed flask and treated with 2,5-dimethoxytetrahydrofuran (6.3 mL, 49.8 mmol). The resulting mixture was heated to 110° C. for 4 hours. TLC analysis indicated complete conversion of starting material to product after 4 hours. Thus, the reaction mixture was cooled to ambient temperature, transferred to a separatory funnel and partitioned (CH₂Cl₂//H₂O). The organic phase was washed with H₂O (3×50 mL), brine (3×50 mL), dried over Na₂SO₄ and evaporated in vacuo to give a light brown residue. The residue was purified by flash chromatography (hexanes→1:9 EtOAc/hexanes) to afford the title compound as a light yellow solid (7.2 g, 78%).

¹H NMR (DMSO-d₆, 300 MHz) 8.34 (dd, 1H), 8.16-8.20 (m, 1H), 7.69 (t, 1H), 7.27 (d, 2H), 6.32 (d, 2H) ppm; MS (ES) 207 (M+H).

Preparation 2

Synthesis of 1-(2-fluoro-5-nitrophenyl)-1H-pyrrole-2-carbaldehyde (P-2)

Anhydrous DMF (0.82 mL, 10.67 mmol) and POCl₃ (0.96 mL, 10.67 mmol) were combined at 0° C. in a 50 mL round bottomed flask. The suspension was warmed to ambient temperature and treated with 1-(2-fluoro-5-nitrophenyl)-1H-pyrrole (2.0 g, 9.7 mmol) as a light yellow solution in anhydrous DMF (8 mL). The resulting mixture was vigorously stirred at room temperature for 5 hours. TLC analysis of the mixture after 5 hours showed the complete conversion of the starting material to the product. The reaction mixture ¹H NMR (DMSO-d₆, 300 MHz) 9.53 (s, 1H), 8.40 (dd, 1H), 7.70 (t, 1H), 7.51 (s, 1H), 7.32 (d, 1H), 6.54 (t, 1H); MS (ES) 235 (M+H).

Preparation 3

Synthesis of 8-nitro-4H-benzo[b]pyrrolo[1,2-d][1,4]oxazine (P-3)

1-(2-fluoro-5-nitrophenyl)-1H-pyrrole-2-carbaldehyde (3.95 g, 16.9 mmol) was suspended in ethanol (100 mL) in a 250 mL round bottomed flask and treated with sodium borohydride (767 mg, 20.3 mmol, 1.2 equiv.). The resulting mixture was stirred at 60° C. for 5 hours. The reaction mixture was cooled to ambient temperature, transferred to a separatory funnel and partitioned (CH₂Cl₂//H₂O). The organic phase was washed with H₂O (3×50 mL), brine (3×50 mL), dried over Na₂SO₄ and evaporated in vacuo to give a light yellow residue. The residue was purified by flash chromatography (hexanes 1:9 EtOAc/hexanes) to afford the title compound as a light yellow solid (2.5 g, 68%).

¹H NMR (DMSO-d₆, 300 MHz) 8.53 (d, 1H), 7.96 (dd, 1H), 7.77 (s, 1H), 7.26 (d, 1H), 6.35 (t, 1H), 6.14 (s, 1H), 5.33 (s, 2H); MS (ES) 217 (M+H).

Preparation 4

Synthesis of 4H-benzo[b]pyrrolo[1,2-d][1,4]oxazin-8-amine (P-4)

¹H NMR (DMSO-d₆, 300 MHz) 7.21 (t, 1H), 6.76 (s, 1H), 6.74 (d, 1H), 6.29 (dd, 1H), 6.23 (t, 1H), 6.01 (s, 1H), 4.97 (s, 2H), 4.88 (s, 2H); MS (ES) 187 (M+H).

Example 1

Synthesis of N2-(4H-benzo[b]pyrrolo[1,2-d][1,4]oxazin-8-yl)-5-fluoro-N4-(1,2,2,6,6-pentamethylpiperidin-4-yl)pyrimidine-2,4-diamine (Compound 1-4)

$^1$H NMR (DMSO-d$_6$, 300 MHz) 8.88 (s, 1H), 8.34 (s, 1H), 7.85 (d, 1H), 7.46 (d, 1H), 7.18-7.19 (m, 2H), 6.86 (d, 1H), 6.23-6.28 (m, 2H), 6.05 (s, 1H), 5.05 (s, 2H), 4.35-4.40 (m, 1H), 1.78 (d, 2H), 1.35 (t, 2H), 1.20 (s, 6H), 1.17 (s, 6H); MS (ES) 437 (M+H).

Example 2

Spectral data for N2-(4H-benzo[b]pyrrolo[1,2-d][1,4]oxazin-8-yl)-5-fluoro-N4-(2,2,6,6-tetramethylpiperidin-4-yl)pyrimidine-2,4-diamine (Compound 1-3)

$^1$H NMR (DMSO-d$_6$, 300 MHz) 8.83 (s, 1H), 7.83 (d, 1H), 7.66 (d, 1H), 7.52 (dd, 1H), 7.23 (s, 1H), 7.14 (d, 1H), 6.86 (d, 1H), 6.25 (t, 1H), 6.05 (s, 1H), 5.06 (s, 2H), 4.31-4.33 (m, 1H), 2.15 (s, 3H), 1.67 (dd, 2H), 1.43 (t, 2H), 1.05 (s, 6H), 0.97 (s, 6H); MS (ES) 451 (M+H).

Examples 3-6

Example 3

Synthesis of N2-(4H-benzo[b]tetrazolo[1,5-d][1,4]oxazin-8-yl)-5-fluoro-N4-((1,2,2,5,5-pentamethylpyrrolidin-3-yl)methyl)pyrimidine-2,4-diamine $^1$H NMR (DMSO-d6, 300 MHz) 9.36 (s, 1H), 8.59 (s, 1H), 7.85 (s, 1H), 7.59 (d, 1H), 7.48 (s, br, 1H), 7.15 (d, 1H), 5.77 (s, 2H), 2.19 (m, 1H), 2.15 (s, 3H), 1.85 (m, 1H), 1.45 (t, 1H), 1.20 (dd, 2H), 1.05 (s, 6H), 0.92 (s, 3H), 0.80 (s, 3H) ppm; MS (ES) 454.52 (M+H).

Example 4

Synthesis of N2-(4H-benzo[b]tetrazolo[1,5-d][1,4]oxazin-8-yl)-5-fluoro-N4-((2,2,5,5-tetramethylpyrrolidin-3-yl)methyl)pyrimidine-2,4-diamine $^1$H NMR (DMSO-d6, 300 MHz) 9.39 (s, 1H), 8.60 (s, 1H), 7.88 (s, 1H), 7.55 (d, 1H), 7.45 (s, br, 1H), 7.19 (d, 1H), 5.75 (s, 2H), 3.48 (m, br, 1H), 2.10 (m, 1H), 1.90 (m, 1H), 1.65 (m, 1H), 1.30 (dd, 2H), 1.20 (s, 6H), 1.15 (s, 3H), 1.10 (s, 3H) ppm; MS (ES) 440.49 (M+H).

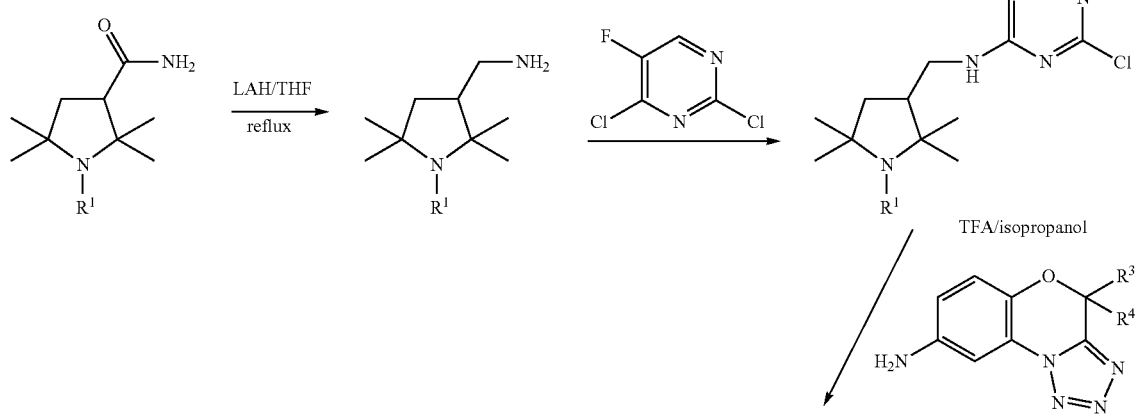

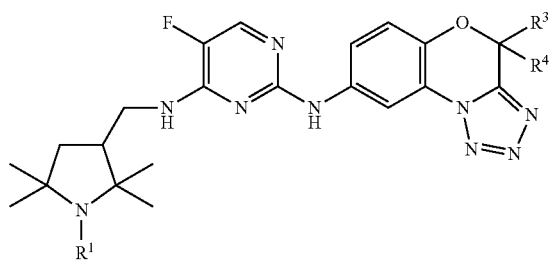

$R^1$ = ―CH$_3$; $R^3$ & $R^4$ = ―H    Example 3
$R^1$ = ―H; $R^3$ & $R^4$ = ―H    Example 4
$R^1$ = ―CH$_3$; $R^3$ & $R^4$ = ―CH$_3$    Example 5
$R^1$ = ―H; $R^3$ & $R^4$ = ―CH$_3$    Example 6

Example 5

Synthesis of N2-(4,4-dimethyl-4H-benzo[b]tetrazolo[1,5-d][1,4]oxazin-8-yl)-5-fluoro-N4-((1,2,2,5,5-pentamethylpyrrolidin-3-yl)methyl)pyrimidine-2,4-diamine $^1$H NMR (DMSO-d6, 300 MHz) 9.32 (s, 1H), 8.60 (s, 1H), 7.88 (s, 1H), 7.58 (d, 1H), 7.44 (s, br, 1H), 7.10 (d, 1H), 3.50 (m, 1H), 2.10 (m, 1H), 2.05 (s, 3H), 1.80 (m, 1H), 1.72 (s, 6H), 1.42 (t, 1H), 1.04 (m, 1H), 1.00 (s, 6H), 0.92 (s, 3H), 0.80 (s, 3H) ppm; MS (ES) 482.57 (M+H).

Example 6

Synthesis of N2-(4,4-dimethyl-4H-benzo[b]tetrazolo[1,5-d][1,4]oxazin-8-yl)-5-fluoro-N4-((2,2,5,5-tetramethylpyrrolidin-3-yl)methyl)pyrimidine-2,4-diamine $^1$H NMR (DMSO-d6, 300 MHz) 9.34 (s, 1H), 8.62 (s, 1H), 7.88 (s, 1H), 7.56 (d, 1H), 7.46 (s, br, 1H), 7.12 (d, 1H), 3.45 (m, 1H), 2.24 (m, 1H), 1.80 (m, 1H), 1.70-1.75 (m, 7H), 1.56 (t, 2H), 1.09 (s, 3H), 1.06 (s, 3H), 1.02 (s, 3H), 0.95 (s, 3H) ppm; MS (ES) 468.54 (M+H).

Examples 7-8

Compounds 1-1 and 1-2 were synthesized according to the following scheme:

Example 7

Synthesis of N2-(4H-benzo[b]tetrazolo[1,5-d][1,4]oxazin-8-yl)-5-fluoro-N4-(2,2,6,6-tetramethylpiperidin-4-yl)pyrimidine-2,4-diamine (Compound 1-1)

$^1$H NMR (DMSO-$d_6$, 300 MHz) 8.65 (d, 1H), 8.26 (d, 1H), 8.01 (d, 1H), 7.81 (bs, 1H), 7.76 (bs, 1H), 7.63 (dd, 1H), 7.19 (d, 1H), 5.72 (s, 2H), 4.47 (m, 1H), 2.05-1.85 (d, 2H), 1.65-1.51 (t, 2H), 1.42 (d, 12H) ppm; MS (ES) 440 (M+H) 9

Example 8

Synthesis of N2-(4H-benzo[b]tetrazolo[1,5-d][1,4]oxazin-8-yl)-5-fluoro-N4-(1,2,2,6,6-pentamethylpiperidin-4-yl)pyrimidine-2,4-diamine (Compound 1-2)

$^1$H NMR (DMSO-$d_6$, 300 MHz) 9.51 (s, 1H), 8.32 (s, 1H), 8.01 (d, 1H), 7.91 (d, 1H), 7.36 (d, 1H), 7.09 (d, 1H), 5.72 (s, 2H), 4.47 (m, 1H), 2.28 (s, 3H), 2.11-2.05 (d, 2H), 1.85-1.71 (t, 2H), 1.35 (d, 12H) ppm; MS (ES) 454 (M+H).

Compounds 1-7 and 1-8 were prepared in similar fashion to Compounds 1-1 and 1-2 as illustrated above.

Examples 9 and 10

This Example describes the synthesis of Compounds 1-11 and 1-12. The synthesis is analogous to that set forth in Examples 7 and 8. The following scheme outlines the synthesis used for these compounds:

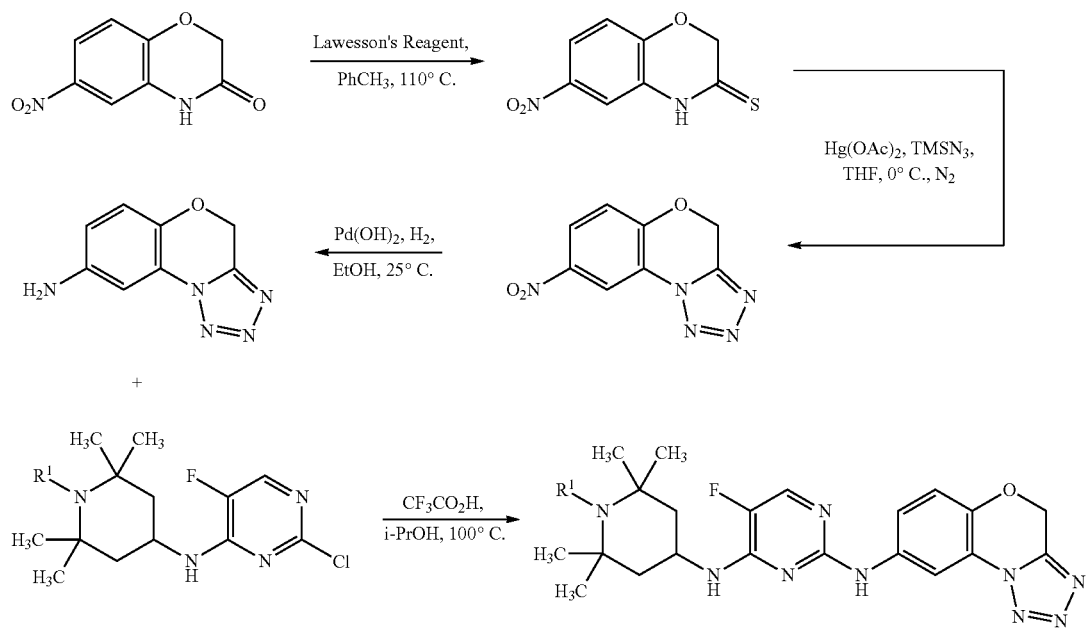

$R^1$ = ——H  Example 7
$R^1$ = ——$CH_3$  Example 8

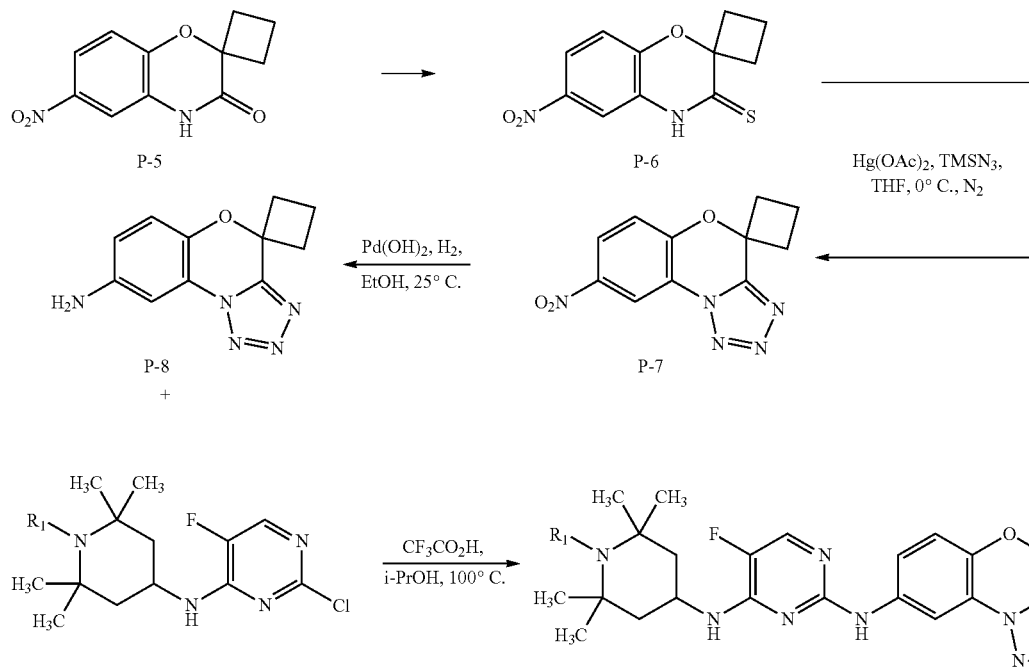

Preparation 5

Synthesis of 2,1-Spiro-butane-6-nitro-2H-benzo[b][1,4]oxazine-3(4H)-one (P-5)

$^1$H NMR (DMSO, 300 MHz) 11.0 (s, 1H), 8.4-8.1 (d, J=8.7 Hz, 1H), 7.7 (s, 1H), 7.21-7.18 (d, J=8.7 Hz, 1H), 2.54 (bs, 2H), 2.34-2.24 (m, 2H), 1.96-1.89 (m, 1H), 1.84-1.75 (m, 1H) ppm; MS (ES) 235.23 (M+H)

Preparation 6

Synthesis of 2,1-Spiro-butane-6-nitro-2H-benzo[b][1,4]oxazine-3(4H)-thione (P-6)

$^1$H NMR (DMSO, 300 MHz) 7.95-7.93 (d, J=8.7 Hz, 1H), 7.89 (s, 1H), 7.29-7.26 (d, J=9.0 Hz, 1H), 2.78-2.71 (m, 2H), 2.4-2.3 (m, 2H), 1.99-1.85 (m, 2H) ppm; MS (ES) 251.23 (M+H)

Preparation 7

Synthesis of 2,1-Spiro-butane-8-nitro-4H-tetrazolo[5,1-c][1,4]benzoxazine (P-7)

$^1$H NMR (DMSO, 300 MHz) 8.57 (s, 1H), 8.29-8.26 (d, J=9.3 Hz, 1H), 7.5-7.47 (d, J=9.0 Hz, 1H), 2.78-2.73 (t, J=8.1 Hz, 4H), 2.1-2.05 (m, 2H) ppm; MS (ES) 260.27 (M+H)

Preparation 8

Synthesis of 8-Amino-2,1-spiro-butane-4H-tetrazolo[5,1-c][1,4]benzoxazine (P-8)

$^1$H NMR (DMSO, 300 MHz) 7.09 (s, 1H), 7.0-6.97 (d, J=8.7 Hz, 1H), 6.59-6.56 (d, J=9.0 Hz, 1H), 5.36 (s, 2H), 2.61-2.55 (m, 4H), 2.02-1.96 (m, 2H) ppm; MS (ES) 230.24 (M+H)

Example 9

Synthesis of N2-{2,1-Spiro-butane-4H-tetrazolo[5,1-c][1,4]benzoxazin-8-yl}-5-fluoro-N4-(1,2,2,6,6-pentamethylpiperidin-4-yl)-2,4-pyrimidinediamine (Compound 1-12)

$^1$H NMR (DMSO, 300 MHz) 9.25 (s, 1H), 8.24 (s, 1H), 7.88-7.87 (d, J=3.6 Hz, 1H), 7.77-7.74 (d, J=9.0 Hz, 1H), 7.23-7.2 (d, J=8.4 Hz, 1H), 7.13-7.1 (d, J=8.7 Hz, 1H), 4.36 (bs, 1H), 2.66-2.61 (t, J=8.1 Hz, 4H), 2.13 (s, 3H), 2.05-2.02 (m, 2H), 1.7-1.67 (d, J=10.2 Hz, 2H), 1.47-1.39 (t, J=12.3 Hz, 2H), 1.04 (s, 6H), 0.97 (s, 6H) ppm; MS (ES) 495.58 (M+H)

Example 10

Synthesis of N2-{2,1-Spiro-butane-4H-tetrazolo[5,1-c][1,4]benzoxazin-8-yl}-5-fluoro-N4-(2,2,6,6-tetramethylpiperidin-4-yl)-2,4-pyrimidinediamine (Compound 1-13)

$^1$H NMR (DMSO, 300 MHz) 9.25 (s, 1H), 8.24 (s, 1H), 7.88-7.86 (d, J=3.9 Hz, 1H), 7.76-7.73 (d, J=9.0 Hz, 1H), 7.23-7.2 (d, J=8.7 Hz, 1H), 7.13-7.1 (d, J=9.0 Hz, 1H), 4.38 (bs, 1H), 2.65-2.6 (t, J=7.5, 4H), 2.03-2.01 (m, 2H), 1.71-1.68 (d, J=9.9 Hz, 2H), 1.19-1.14 (t, J=7.5 Hz, 2H), 1.1 (s, 6H), 1.01 (s, 6H) ppm; MS (ES) 480.50 (M+H)

Examples 11-12

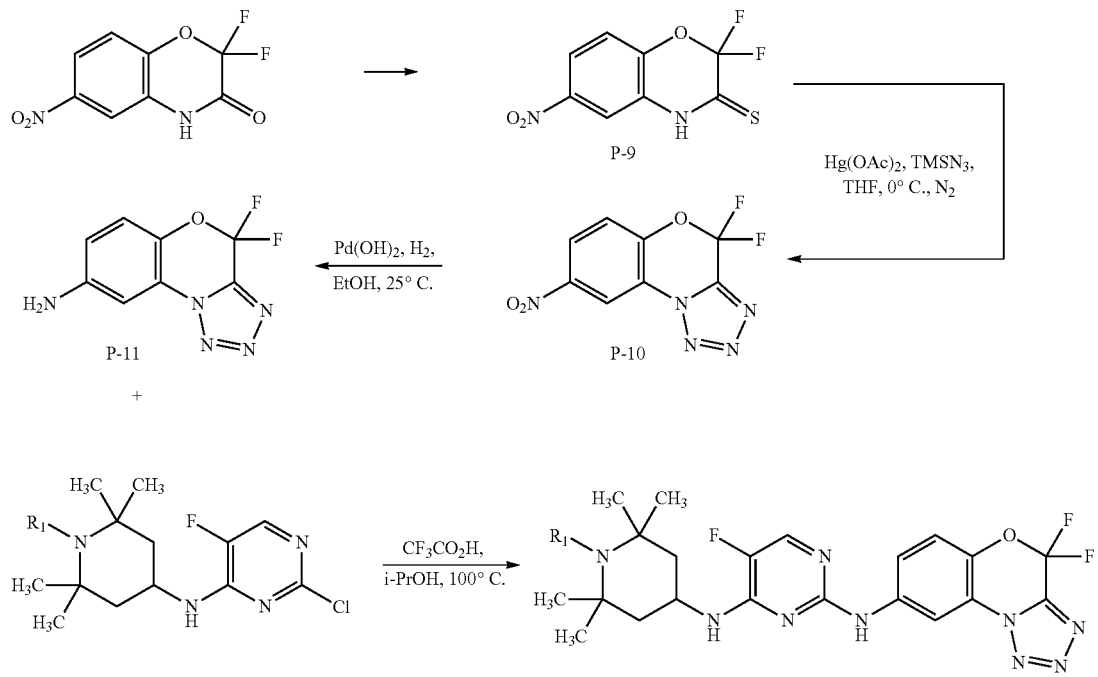

R¹ = —CH₃ Example 11
R¹ = —H   Example 12

Preparation 9

Synthesis of 2,2-difluoro-6-nitro-2H-benzo[b][1,4]oxazine-3(4H)-thione (P-9)

¹H NMR (DMSO, 300 MHz) 8.1-8.07 (d, J=9.0 Hz, 1H), 8.05-8.04 (d, J=2.7 Hz, 1H), 7.63-7.6 (d, J=9.0 Hz, 1H) ppm; MS (ES) 247.18 (M+H)

Preparation 10

Synthesis of 4,4-difluoro-8-nitro-4H-benzo[b]tetrazolo[1,5-d][1,4]oxazine (P-10)

¹H NMR (DMSO, 300 MHz) 8.82 (s, 1H), 8.49-8.46 (d, J=9.3 Hz, 1H), 7.95-7.92 (d, J=9.0 Hz, 1H) ppm; MS (ES) 256.12 (M+H)

Preparation 11

Synthesis of 4,4-difluoro-4H-benzo[b]tetrazolo[1,5-d][1,4]oxazin-8-amine (P-11)

¹H NMR (DMSO, 300 MHz) 7.3-7.27 (d, J=9.0 Hz, 1H), 7.26 (s, 1H), 6.75-6.72 (d, J=9.0 Hz, 1H), 5.7 (s, 2H) ppm; MS (ES) 226.19 (M+H)

Example 11

Synthesis of N2-(4,4-difluoro-4H-benzo[b]tetrazolo[1,5-d][1,4]oxazin-8-yl)-5-fluoro-N4-(1,2,2,6,6-pentamethylpiperidin-4-yl)pyrimidine-2,4-diamine ¹H NMR (DMSO, 300 MHz) 9.45 (s, 1H), 8.5 (s, 1H), 7.98-7.92 (m, 2H), 7.47-7.44 (d, J=9.0 Hz, 1H), 7.31-7.29 (d, J=7.5 Hz, 1H), 4.36 (bs, 1H), 2.18 (s, 3H), 1.73-1.69 (d, J=11.7 Hz, 2H), 1.51-1.43 (t, J=11.7 Hz, 2H), 1.07 (s, 6H), 1.03 (s, 6H) ppm; MS (ES) 490.07 (M+H)

Example 12

Synthesis of N2-(4,4-difluoro-4H-benzo[b]tetrazolo[1,5-d][1,4]oxazin-8-yl)-5-fluoro-N4-(2,2,6,6-tetramethylpiperidin-4-yl)pyrimidine-2,4-diamine ¹H NMR (DMSO, 300 MHz) 9.47 (s, 1H), 8.52 (s, 1H), 7.95-7.92 (m, 2H), 7.49-7.46 (d, J=9.0 Hz, 1H), 7.42-7.39 (d, J=8.4 Hz, 1H), 4.46 (bs, 1H), 1.82-1.76 (d, J=9.9 Hz, 2H), 1.38-1.3 (t, J=12.3 Hz, 2H), 1.26 (s, 6H), 1.16 (s, 6H) ppm; MS (ES) 476.10 (M+H)

Examples 13-14

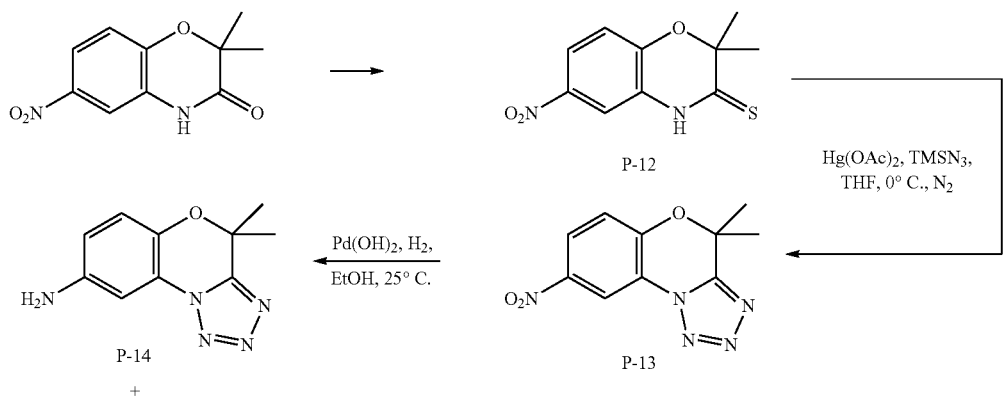

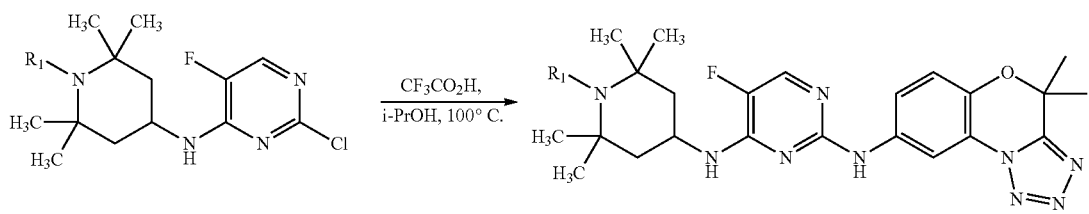

R¹ = —CH₃ Example 13
R¹ = —H Example 14

Preparation 12

Synthesis of 2,2-dimethyl-6-nitro-2H-benzo[b][1,4]oxazine-3(4H)-thione (P-12)

¹H NMR (DMSO, 300 MHz) 7.95-7.92 (m, 2H), 7.19-7.17 (d, J=8.1 Hz, 1H), 1.59 (s, 6H) ppm; MS (ES) 239.20 (M+H)

Preparation 13

Synthesis of 4,4-dimethyl-8-nitro-4H-benzo[b]tetrazolo[1,5-d][1,4]oxazine (P-13)

¹H NMR (DMSO, 300 MHz) 8.6 (s, 1H), 8.3-8.27 (d, J=9.3 Hz, 1H), 7.48-7.45 (d, J=9.0 Hz, 1H), 1.83 (s, 6H) ppm; MS (ES) 248.22 (M+H)

Preparation 14

Synthesis of 4,4-dimethyl-4H-benzo[b]tetrazolo[1,5-d][1,4]oxazin-8-amine (P-14)

¹H NMR (DMSO, 300 MHz) 7.1 (s, 1H), 6.94-6.91 (d, J=8.7 Hz, 1H), 6.59-6.57 (d, J=8.7 Hz, 1H), 5.34 (s, 2H), 1.67 (s, 6H) ppm; MS (ES) 218.28 (M+H)

Example 13

Synthesis of N2-(4,4-dimethyl-4H-benzo[b]tetrazolo[1,5-d][1,4]oxazin-8-yl)-5-fluoro-N4-(1,2,2,6,6-pentamethylpiperidin-4-yl)pyrimidine-2,4-diamine ¹H NMR (DMSO, 300 MHz) 9.25 (s, 1H), 8.27 (s, 1H), 7.88-7.86 (d, J=3.9 Hz, 1H), 7.74-7.71 (d, J=9.0 Hz, 1H), 7.21-7.19 (d, J=7.8 Hz, 1H), 7.08-7.05 (d, J=9.0 Hz, 1H), 4.35 (bs, 1H), 2.12 (s, 3H), 1.72-1.67 (m, 8H), 1.47-1.39 (t, J=12.3 Hz, 2H), 1.04 (s, 6H), 0.95 (s, 6H) ppm; MS (ES) 482.34 (M+H)

Example 14

Synthesis of N2-(4,4-dimethyl-4H-benzo[b]tetrazolo[1,5-d][1,4]oxazin-8-yl)-5-fluoro-N4-(2,2,6,6-tetramethylpiperidin-4-yl)pyrimidine-2,4-diamine $^1$H NMR (DMSO, 300 MHz) 9.25 (s, 1H), 8.27 (s, 1H), 7.88-7.87 (d, J=3.6 Hz, 1H), 7.74-7.7 (d, J=9.3 Hz, 1H), 7.25-7.22 (d, J=8.1 Hz, 1H), 7.08-7.05 (d, J=9.0 Hz, 1H), 4.39 (bs, 1H), 1.71 (bs, 8H), 1.23-1.14 (t, J=12.6 Hz, 2H), 1.11 (s, 6H), 1.04 (s, 6H) ppm; MS (ES) 468.10 (M+H)

Example 15

Assays of Exemplary Compounds

Several subject compounds were tested according to procedures in the "Characterization of Functional Properties" section. PKC kinase activity was measured using the procedure Section A.1 (Protein Kinase C assay) with the appropriate isoform. The whole cell assay was run according to the procedure in Section A.2 (IL-2 ELISA, Human primary T cell, anti-CD3+CD28+ Assays). Assay data for certain compounds from Tables 1 and 2 are listed below in Table 5, in which "A" indicates an IC$_{50}$ in the indicated assay of less than 0.25 1 µM; "B" is 0.25 to 0.5 µM; "C" is 0.5 to 1 µM; and "D" is from 1 µM to 5 µM. Blank entries indicate that the IC$_{50}$ was not determined.

TABLE 5

| Compound | Whole cell assay | PKC-alpha | PKC-beta | PKC-delta | PKC-epsilon | PKC-theta |
|---|---|---|---|---|---|---|
| 1-1 | A | A | A | A | A | A |
| 1-2 | A | A | A | A | A | A |
| 1-3 | D | | | | | |
| 1-4 | D | | | | | |
| 1-5 | C | A | A | A | A | A |
| 1-6 | B | A | A | A | A | A |
| 1-7 | A | A | A | A | A | A |
| 1-8 | A | A | A | A | A | A |
| 1-9 | C | | | | | |
| 1-10 | A | | | | | |
| 1-11 | A | A | A | A | A | A |
| 1-12 | A | A | A | A | A | A |
| 1-17 | A | A | A | A | A | A |
| 1-18 | A | A | A | A | A | A |
| 2-1 | A | A | A | A | A | A |
| 2-2 | A | A | A | A | A | A |
| 2-7 | A | A | A | A | A | A |
| 2-8 | B | A | B | A | A | A |
| 2-13 | A | A | A | A | A | A |
| 2-14 | A | A | A | A | A | A |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound selected from the group consisting of:
   N2-(4,4-dimethyl-4H-benzo[b]tetrazolo[1,5-d][1,4]oxazin-8-yl)-5-fluoro-N4-(2,2,6,6-tetramethylpiperidin-4-yl)pyrimidine-2,4-diamine; and
   N2-(4,4-dimethyl-4H-benzo[b]tetrazolo[1,5-d][1,4]oxazin-8-yl)-5-fluoro-N4-(1,2,2,6,6-pentamethylpiperidin-4-yl)pyrimidine-2,4-diamine,
   or a salt or stereoisomer thereof.

2. The compound of claim 1, wherein the compound is:
   N2-(4,4-dimethyl-4H-benzo[b]tetrazolo[1,5-d][1,4]oxazin-8-yl)-5-fluoro-N4-(2,2,6,6-tetramethylpiperidin-4-yl)pyrimidine-2,4-diamine.

3. The compound of claim 1, wherein the compound is:
   N2-(4,4-dimethyl-4H-benzo[b]tetrazolo[1,5-d][1,4]oxazin-8-yl)-5-fluoro-N4-(1,2,2,6,6-pentamethylpiperidin-4-yl)pyrimidine-2,4-diamine.

4. A pharmaceutical composition comprising a compound of claim 1 and a pharmaceutically acceptable carrier.

5. A pharmaceutical composition comprising a compound of claim 2 and a pharmaceutically acceptable carrier.

6. A pharmaceutical composition comprising a compound of claim 3 and a pharmaceutically acceptable carrier.

* * * * *

```
                         SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 1

Arg Phe Ala Arg Lys Gly Ser Leu Arg Gln Lys Asn Val
 1               5                  10
```